(12) United States Patent
Ahluwalia

(10) Patent No.: US 10,532,149 B2
(45) Date of Patent: *Jan. 14, 2020

(54) SUCTION DEVICE

(71) Applicant: Prabhat K. Ahluwalia, Little Falls, NY (US)

(72) Inventor: Prabhat K. Ahluwalia, Little Falls, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/614,136

(22) Filed: Jun. 5, 2017

(65) Prior Publication Data

US 2017/0266363 A1  Sep. 21, 2017

Related U.S. Application Data

(63) Continuation of application No. 15/416,190, filed on Jan. 26, 2017, now Pat. No. 9,750,867, which is a continuation of application No. 15/147,871, filed on May 5, 2016, now Pat. No. 9,592,333, which is a continuation of application No. 12/904,573, filed on Oct. 14, 2010, now Pat. No. 9,358,328.

(60) Provisional application No. 61/286,533, filed on Dec. 15, 2009.

(51) Int. Cl.
*A61M 3/02* (2006.01)
*A61M 1/00* (2006.01)
*A61M 25/00* (2006.01)

(52) U.S. Cl.
CPC .......... *A61M 3/0283* (2013.01); *A61M 1/008* (2013.01); *A61M 1/0031* (2013.01); *A61M 1/0039* (2013.01); *A61M 1/0064* (2013.01); *A61M 1/0084* (2013.01); *A61M 1/0086* (2014.02); *A61M 2025/0019* (2013.01); *A61M 2205/502* (2013.01); *A61M 2205/52* (2013.01)

(58) Field of Classification Search
CPC .............. A61M 1/0023; A61M 1/0031; A61M 1/0058; A61M 1/0062; A61M 1/008; A61M 1/0084; A61M 3/0283; A61M 1/0041; A61M 1/0039; A61M 1/0045; A61M 1/0064; B65G 53/28; Y10S 604/902
See application file for complete search history.

(56) References Cited

U.S. PATENT DOCUMENTS

| | | | | |
|---|---|---|---|---|
| 3,771,527 A | * | 11/1973 | Ruisi ................... | A61M 1/0084 604/43 |
| 3,952,743 A | * | 4/1976 | Harrison ............. | A61M 1/0084 604/268 |
| 4,468,217 A | * | 8/1984 | Kuzmick ............. | A61M 1/0039 433/92 |
| 5,244,458 A | * | 9/1993 | Takasu ................ | A61M 1/0056 604/22 |
| 5,449,357 A | * | 9/1995 | Zinnanti ............. | A61B 18/1482 604/21 |
| 5,846,219 A | * | 12/1998 | Vancaillie .............. | A61B 17/42 604/35 |

(Continued)

*Primary Examiner* — Bradley J Osinski
*Assistant Examiner* — Larry R. Wilson
(74) *Attorney, Agent, or Firm* — Pierson IP, PLLC

(57) ABSTRACT

A suction device includes an outer tube having an inlet at a first end and an inner suction tube located within the outer tube, the inner suction tube having an inlet at a first end corresponding to the first end of the outer tube. The inlet of the inner suction tube is offset by a distance from the inlet of the outer suction tube, such that the inlet of the inner suction tube is located within the outer suction tube.

20 Claims, 27 Drawing Sheets

(56) References Cited

U.S. PATENT DOCUMENTS

| | | | | |
|---|---|---|---|---|
| 6,156,004 A | * | 12/2000 | Tremaine | A61M 1/0084 |
| | | | | 604/27 |
| 2001/0037082 A1 | * | 11/2001 | Kamiyama | A61M 1/0062 |
| | | | | 604/43 |
| 2006/0100605 A1 | * | 5/2006 | Bicakci | A61M 1/008 |
| | | | | 604/540 |
| 2008/0091074 A1 | * | 4/2008 | Kumar | A61B 1/00071 |
| | | | | 600/156 |

* cited by examiner

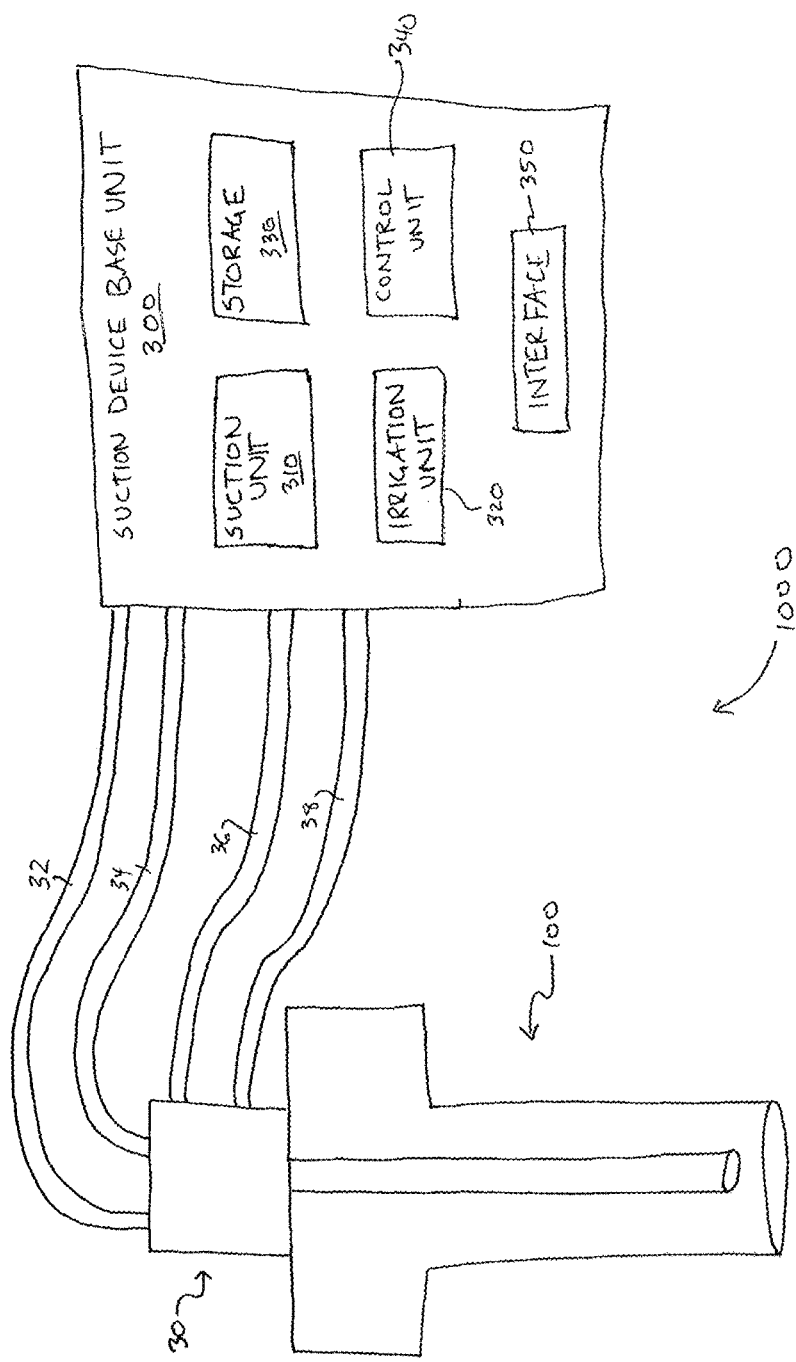

SUCTION DEVICE

CROSS-REFERENCE TO RELATED APPLICATIONS

This U.S. non-provisional patent application claims priority under 35 U.S.C. § 119 of U.S. Provisional Application No. 61/286,533, filed on Dec. 15, 2009, the entire contents of which are hereby incorporated by reference. This application also is a continuation of and claims a benefit under 35 U.S.C. § 120 of prior filed Non-Provisional application Ser. No. 12/904,573 filed on Oct. 14, 2010, the content of which is hereby incorporated by reference

BACKGROUND

1. Field of the Invention

The present disclosure herein relates to a suction device, and more particularly, to a suction device that removes clots from a fluid.

2. Description of the Related Art

Suction devices may be used for medical purposes to remove fluids from an area that needs to be examined by a physician or surgeon or to remove clots and other obstructions from an artery, organ, or other cavity. However, when a conventional suction device sucks a solid object, such as a clot or a hard cluster of cells or other material, the suction device may no longer function to clear the area that needs to be examined. The clot may block the suction inlet, and a physician must remove the suction device from the area to be examined to clean the suction device.

To prevent clogging the inlet, suction devices may utilize an inner tube or cannula positioned within an outer tube to perform suction where the inlet of the inner tube is flush or co-planar with the inlet of the outer tube. The inner tube and outer tubes may include multiple holes near the inlets so that even if the inlet of the outer tube is blocked by a clot, the holes may continue to generate suction to remove fluids.

However, even though providing holes around the inlets allows the suction device to continue operating, it also reduces the suction of the device, thereby making the device less effective.

SUMMARY

The present general inventive concept provides a suction device capable of continuing a suction operation even after a clot blocks an inlet of the suction device.

The present general inventive concept provides a suction device to generate a vacuum in an outer tube using suction from an inner tube offset from an inlet of the outer tube.

Additional features and utilities of the present general inventive concept will be set forth in part in the description which follows and, in part, will be obvious from the description, or may be learned by practice of the general inventive concept.

Features and/or utilities of the present general inventive concept may be realized by a suction device including an outer tube having an inlet at a first end and an inner suction tube located within the outer tube, the inner suction tube having an inlet at a first end corresponding to the first end of the outer tube, wherein the inlet of the inner suction tube is offset by a distance from the inlet of the outer suction tube, such that the inlet of the inner suction tube is located within the outer suction tube.

The outer tube may include a chamber opposite the inlet, the chamber having a diameter different than a diameter of the inlet.

The diameter of the chamber may be larger than the diameter of the inlet.

The chamber may have one of a rectangular shape and a cylindrical shape.

The chamber may include an opening to fit the inner suction tube.

The suction device may further include a valve surrounding the opening to seal the opening when the inner suction tube is located in the opening.

A rim of the inlet of the outer tube may include protrusions located at intervals around the rim, the protrusions extending from the outer tube in a same direction as a length of the outer tube.

The protrusions may have one of a rounded shape and a polygonal shape having rounded corners.

A rim of the inlet of the inner tube may include protrusions located at intervals around the rim, the protrusions extending from the inner tube in a same direction as a length of the inner tube.

The protrusions may have one of a rounded shape and a polygonal shape having rounded corners. Alternatively, the protrusions may have sharp corners.

Side walls of the outer tube between a rim of the inlet of the outer tube and a rim of the inlet of the inner tube may include no openings.

Side walls of the outer tube between a rim of the inlet of the outer tube and a surface of the outer tube at an end of the outer tube opposite the inlet may include no openings.

The side walls of the outer tube may include no openings.

The side walls of the inner tube may include no openings.

The inner suction tube may be permanently fixed to the outer tube.

The inner suction tube may be fixed to the outer tube via at least one of an adhesive, a weld, and a seal.

The inner suction tube may be integral with the outer tube. Alternatively, the inner suction tube may be movable with respect to the outer tube.

The inner suction tube may be removable with respect to the outer tube.

The outer tube may include an opening at an end opposite the intake to receive the inner suction tube.

The inner suction tube may include a tab on an outer surface to stop a movement of the inner suction tube in a direction of the intake of the outer tube before a rim of the inner suction tube reaches the rim of the outer suction tube.

The inner suction tube may be mounted to a side wall of the outer tube. Alternatively, the inner suction tube may be positioned away from each side wall of the outer tube.

At least one of the outer tube and the inner suction tube may be made of one of fiberglass, plastic, nanofibers, and metal.

The distance of the offset may be a fixed distance. Alternatively, the distance of the offset may be adjustable.

The suction device may include spacers positioned between the inner tube and the outer tube to maintain the position of the inner tube with respect to the outer tube.

The inner tube may include two or more inner tubes, each having a separate inlet and a separate outlet. The rims of the inner tubes may each be offset from rim of the outer tube by a different distance. Alternatively, the rims of the inner tubes may be each offset from the rim of the outer tube by the same distance.

Features and/or utilities of the present general inventive concept may also be realized by a suction system including an outer tube having a first inlet at a first end and an inner suction tube located within the outer tube, the inner suction tube having a second inlet at a first end corresponding to the first end of the outer tube and an outlet at an end opposite the second inlet, the outlet connected to a suction base unit. The second inlet of the inner suction tube may be offset by a distance from the first inlet of the outer suction tube, such that the second inlet of the inner suction tube is located within the outer suction tube.

The suction base unit may include an irrigation unit to cause the inner suction tube to perform an irrigation function via the inlet.

Features and/or utilities of the present general inventive concept may also be realized by a suction device including an outer tube having an inlet including a rim and an inner suction tube within the outer tube having an inlet including a rim offset from the rim of the outer tube. The inner suction tube may form a vacuum between a wall of the inner suction tube and a wall of the outer suction tube.

Features and/or utilities of the present general inventive concept may also be realized by a method of performing suction, the method including providing an outer tube having an inlet including a first rim and an inner suction tube having an inlet including a second rim offset within the outer tube from the first rim of the outer tube, and removing air from the outer tube to form a vacuum in the outer tube.

The method may further include submerging the first rim of the outer tube in a fluid.

Removing air from the outer tube may include performing suction via the inlet of the inner suction tube.

BRIEF DESCRIPTION OF THE DRAWINGS

The accompanying drawings are included to provide a further understanding of the general inventive concept and are incorporated in and constitute a part of this specification. The drawings illustrate exemplary embodiments of the general inventive concept and, together with the description, serve to explain principles of the general inventive concept.

FIG. 7 illustrates a suction device base unit according to another embodiment of the present general inventive concept.

DETAILED DESCRIPTION OF THE EMBODIMENTS

Preferred embodiments of the general inventive concept will be described below in more detail with reference to the accompanying drawings. The embodiments of the general inventive concept may, however, be embodied in different forms and should not be constructed as limited to the embodiments set forth herein. Rather, these embodiments are provided so that this disclosure will be thorough and complete, and will fully convey the scope of the general inventive concept to those skilled in the art. Like numbers refer to like elements throughout.

Figure 1A:
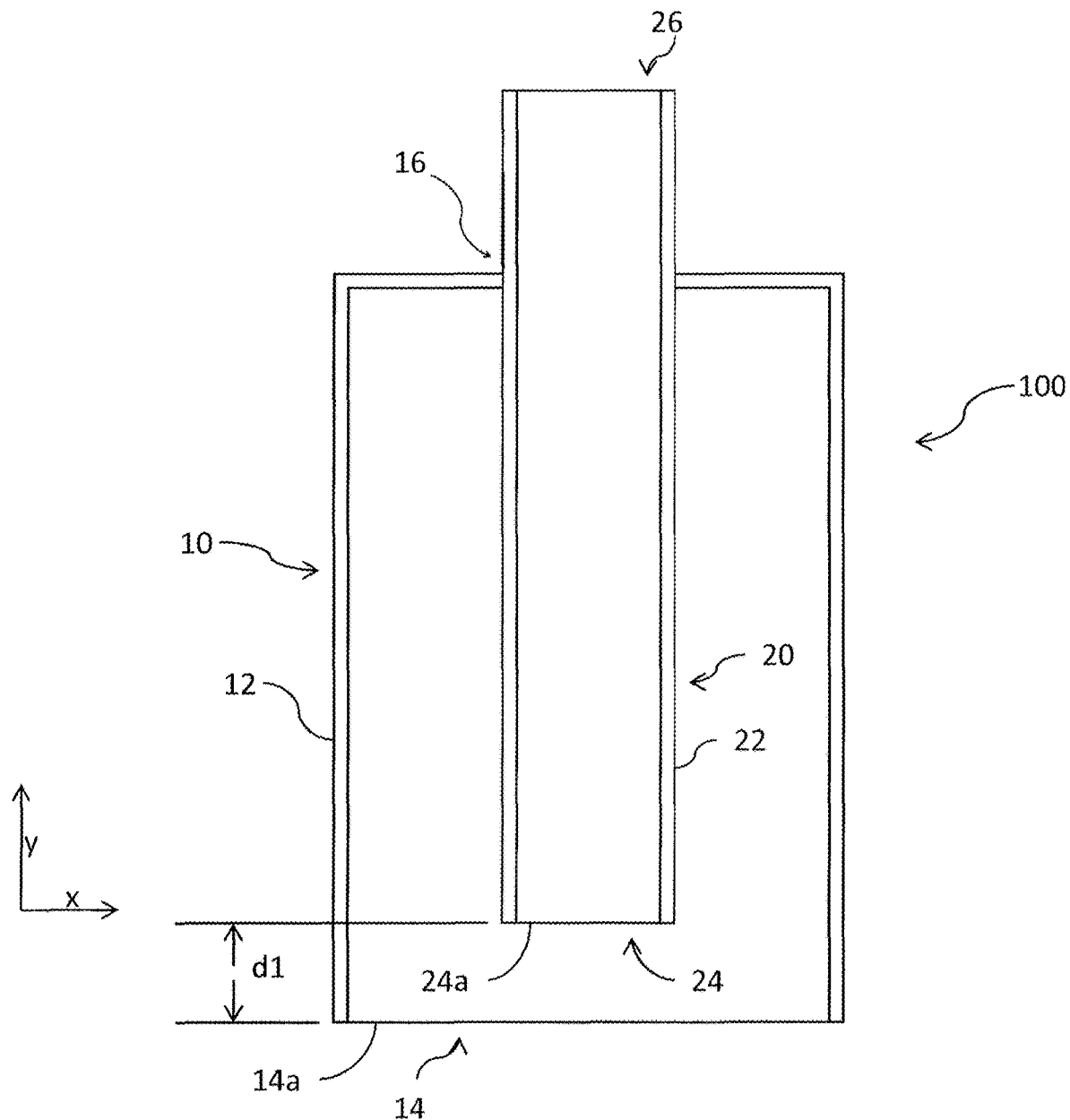
FIG. 1A illustrates a plan view of a suction device according to an embodiment of the present general inventive concept.
Figure 1B:
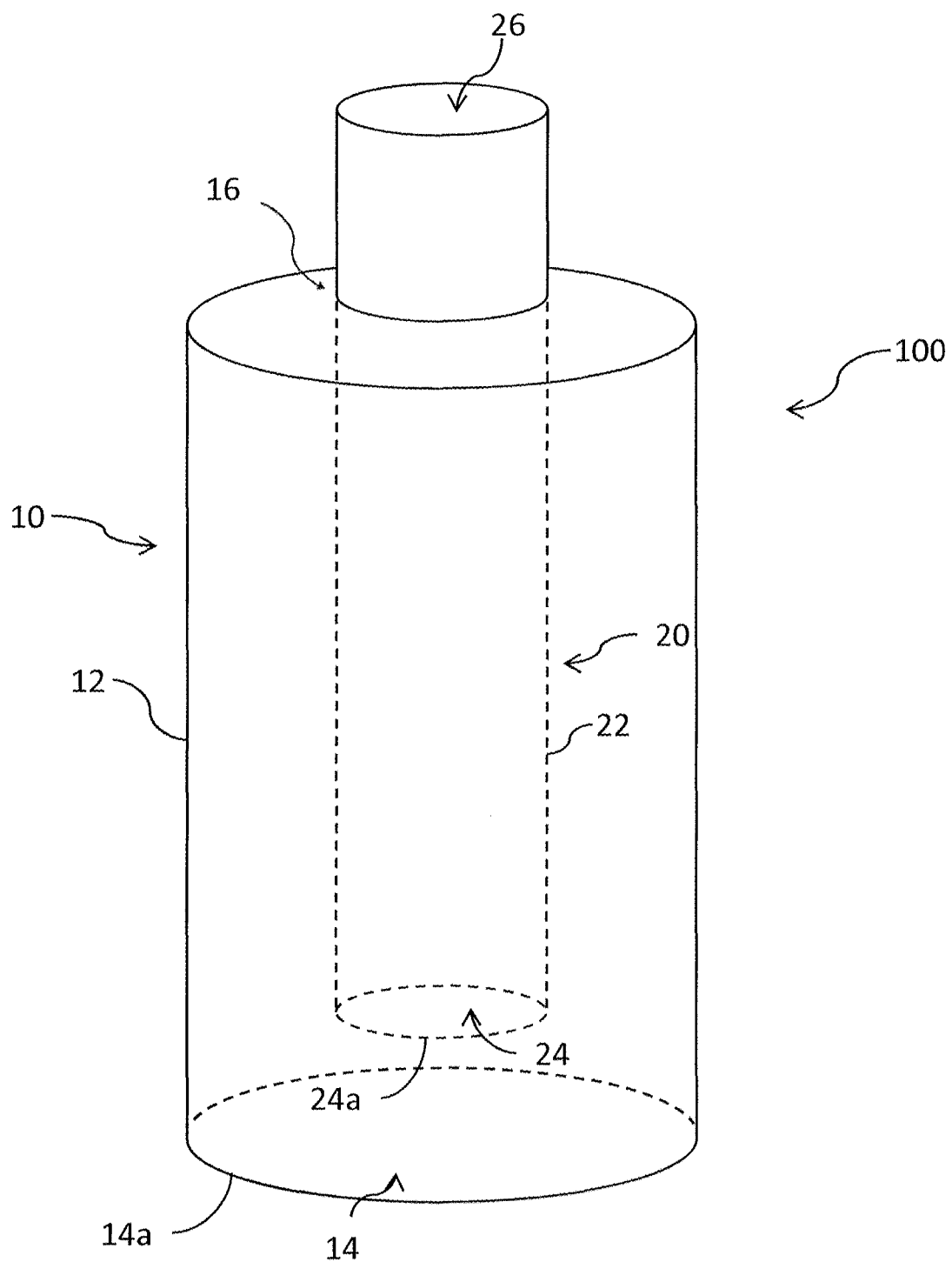
FIG. 1B illustrates a perspective view of the suction device of FIG. 1A.

FIGS. 1A and 1B illustrate a suction device 100 according to an embodiment of the present general inventive concept. The suction device 100 includes an outer tube 10 including a tube portion 12 including an inlet 14 at the end of the tube portion 12. The suction device 100 also includes an inner suction tube 20 having a tube portion 22 and an inlet 24. The inner suction tube 20 may also include an outlet 26 outside the outer tube 10. The outlet 26 may be connected to a vacuum unit or a suction base unit to provide suction to the inner tube 20. A rim 24a of the inner tube 20 is offset by a distance d1 in the direction y from the rim 14a of the outer tube 10.

The inner tube 20 may provide a suction operation, an irrigation operation, or any other appropriate operation. During a suction operation, the inner tube 20 first sucks the air out of the outer tube 10 to generate a vacuum in the outer tube 10 having a strength determined by a volume between the outer tube 10 and inner tube 20. When the inlet 14 of the outer tube 10 is submersed in a fluid, the vacuum of the outer tube 10 draws the fluid up to the inner suction tube 20, which transmits the fluid to a connected suction base unit. In addition, as discussed below, the offset distance d1 of the rim 24a of the inner tube 20 from the rim 14a of the outer tube 10 allows the suction device 100 to prevent blockages caused by clots.

The inner tube 20 fits within the outer tube 10 so that the outer tube 10 is sealed except for the inlet 14. A connection hole or connection portion 16 of the outer tube 10 may be sealed with adhesive, by welding, by a seal structure, or any other appropriate method of sealing the outer tube 10.

Throughout the specification and figures, the inner tube 20 and outer tube 10 are described and illustrated as having no holes or openings in side walls thereof. In particular, the tube portion 12 of the outer tube 10 may have no holes or openings between the respective inlets 14 and 24 to ensure that a vacuum may be generated in the outer tube 10 and that the inlet 24 of the inner tube maintains a suction force.

However, it may be possible to include holes 400, 410 or openings that do not substantially affect the vacuum and suction forces. For example, the holes 400, 410 or openings may be closed during a suction operation to allow the inner tube 10 to generate a vacuum in the outer tube 10. Holes 410 or openings may be located adjacent to the rim 14a of the outer tube 10 below a point where fluid is expected to be located, such that the holes 410 or openings do not affect the generation of the vacuum in the outer tube 10. Additional tubes, suction devices, fluid-providing units, or other devices may be connected to the holes 410 or openings and may be configured to maintain the vacuum in the outer tube 10.

Figure 2A:
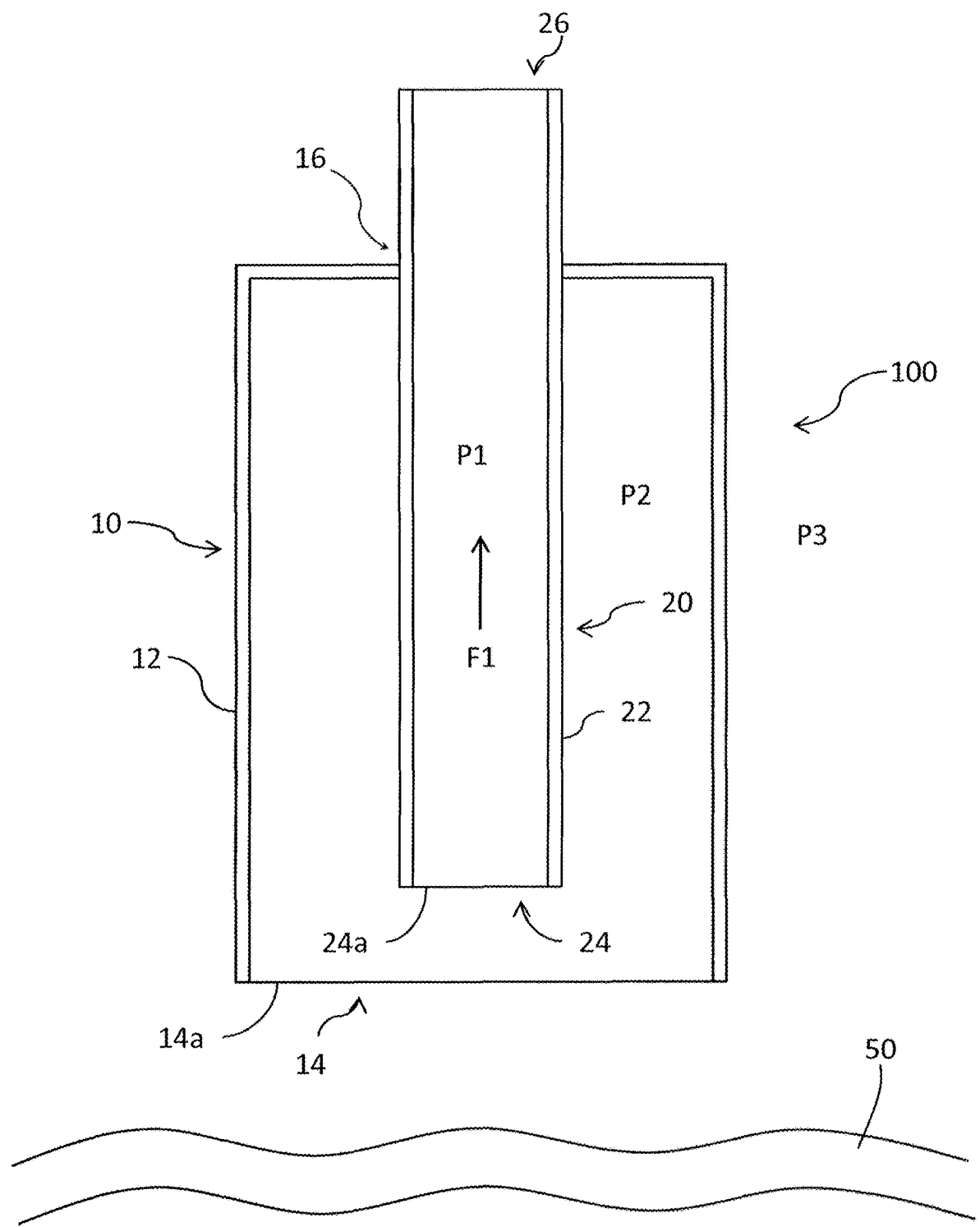
FIGS. 2A to 2E illustrate a suction operation of a suction device according to the present general inventive concept.

FIGS. 2A to 2E illustrate a suction operation using the suction device 100. In FIG. 2A, the suction device 100 is not submersed in a fluid 50. The inner tube 20 generates suction, and since the inlet 24 of the inner tube is located within the outer tube 10, the inner tube 20 sucks the air out of the outer tube 10. When submersed into fluid 50, the suction of the inner tube 20 generates a vacuum in the outer tube 10. The strength of the vacuum is determined by the space or volume between the outer tube 10 and the inner tube 20. A desired volume may be obtained by adjusting the dimensions of the outer tube, the inner tube, and the offset distance between the inner and outer tubes, as described below.

In FIG. 2A, as the inner tube 20 begins generating suction, an air pressure P1 in the inner tube 20 decreases, generating the suction force F1. Initially, the air pressure P2 of the outer tube 10 is the same as the air pressure P3 of the atmosphere outside the suction device 100. However, as the suction proceeds, the pressure P2 of the outer tube 10 decreases until it is the same as, or near, the pressure P1 of the inner tube. This generates an upward suction force F2 into the outer chamber. At this point, the relationship between the air pressures P1, P2, and P3 of the inner tube 20, the outer tube 10, and the atmosphere, respectively, may be P1=P2>P3, or P1≈P2>P3.

Figure 2B:
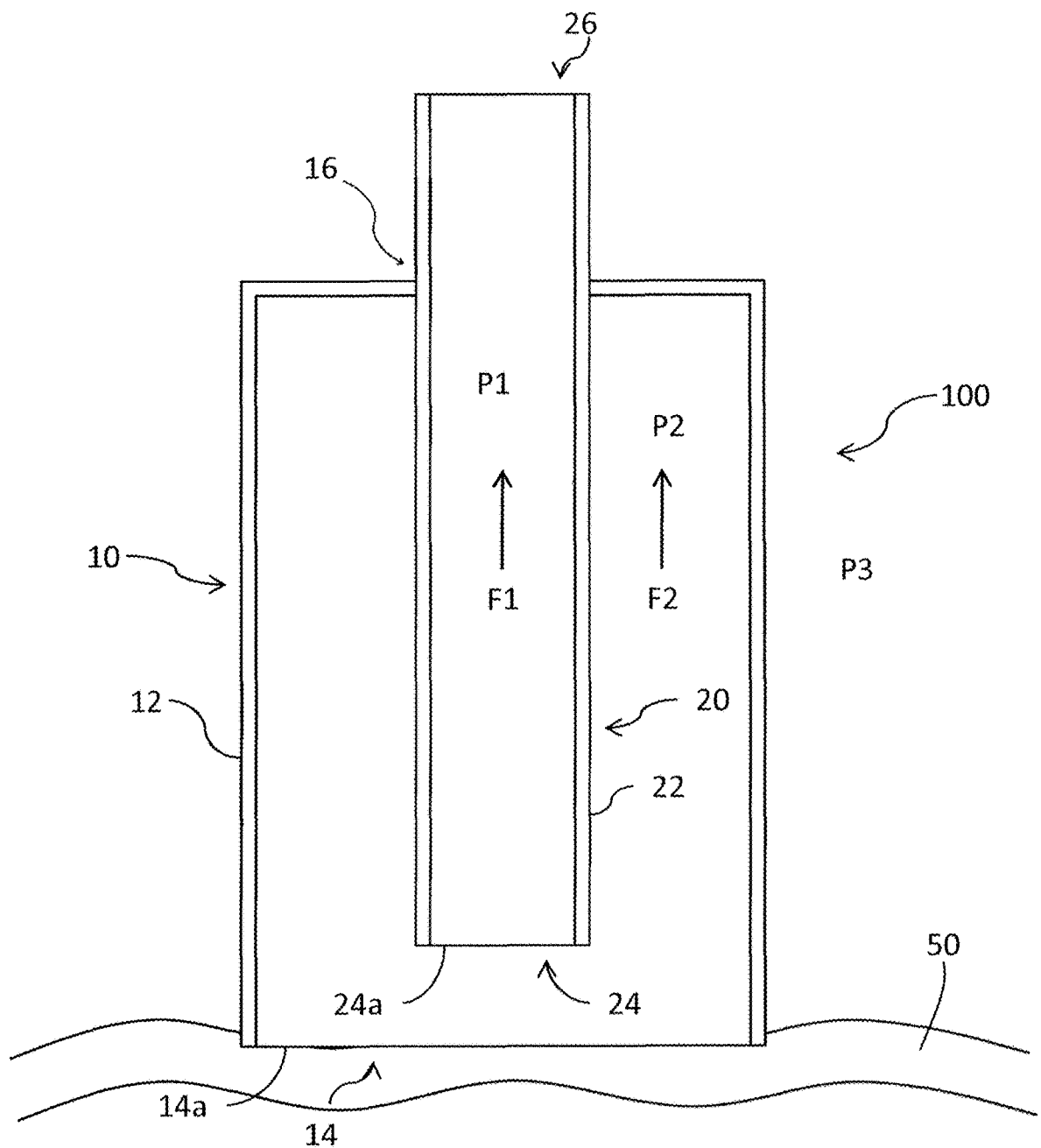

In FIG. 2B, the inlet 14 of the outer tube 10 is submersed in a fluid 50. Although the suction device 100 may be used in any appropriate environment, the fluid may be blood, fat, or any other bodily fluid when the suction device is used as a medical device. For example, the suction device 100 may be used to clear fluid from an area within a body to allow a physician or surgeon to see an operation area.

When the inlet 14 of the outer tube 10 is submerged in the fluid 50, the inner tube 20 generates a vacuum and a corresponding suction force F2 in the outer tube 10. The offset distance d1 of the rim 24a of the inner tube 20 from the rim 14a of the outer tube 10 allows the inner tube to generate the vacuum. Upon submersion, the pressure P1 of the inner tube 20 is the same as the pressure P2 of the outer tube 10, and both the pressure P1 and P2 are less than the atmosphere pressure P3. Accordingly, the suction force F1 in the inner tube 20 is the same as the suction force F2 within the outer tube 10.

Figure 2C:
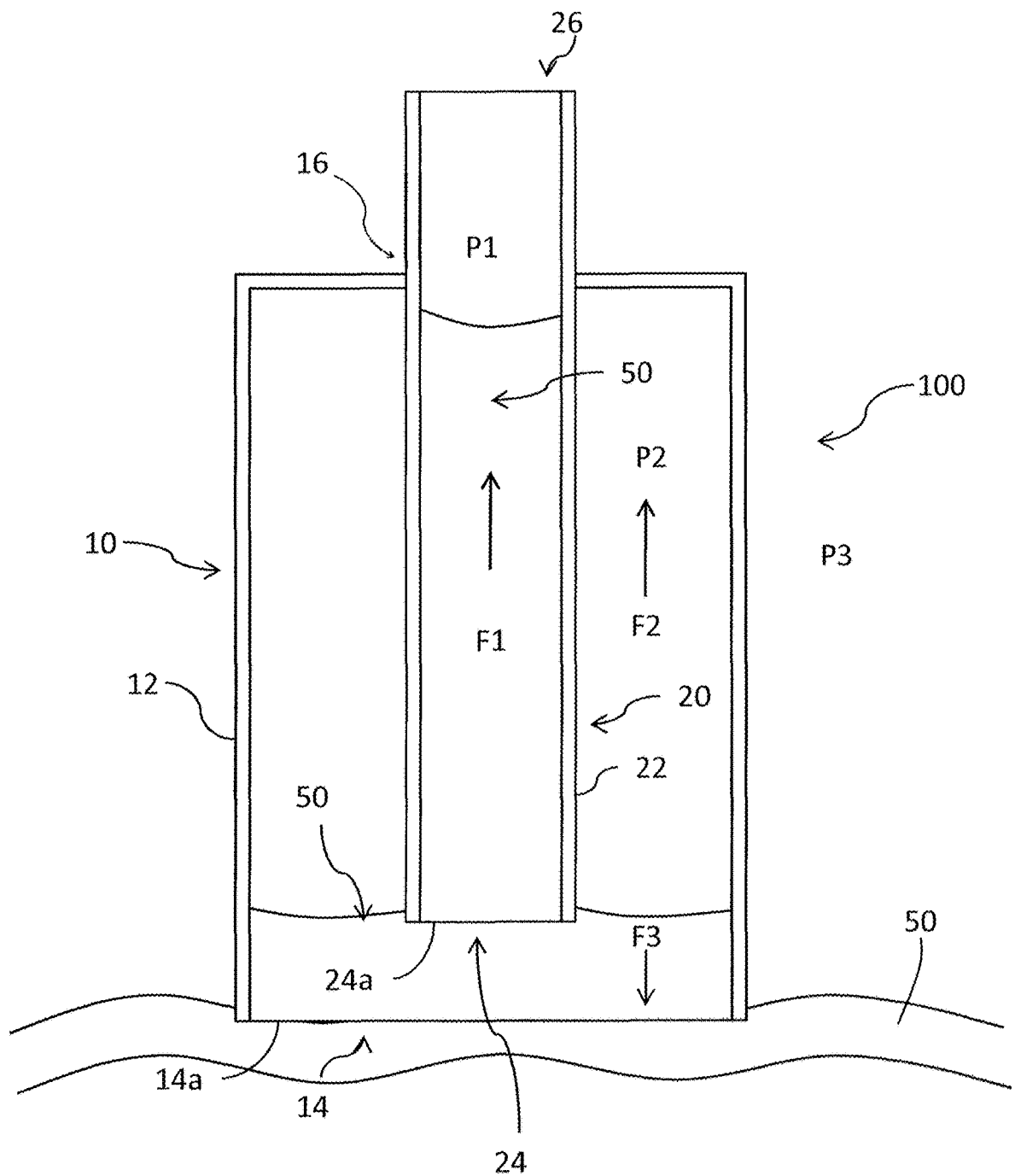

As illustrated in FIG. 2C, when the upward suction force F2 is greater than the fluid's downward force F3, the fluid 50 rises within the outer tube 10. The downward force F3 of the fluid 50 is a function of its density since the weight of the fluid at the inlet 14 of the outer tube 10 and within the outer tube 10 is defined as its volume times its density. The dimensions of suction device 100 may be adjusted so that the inner tube 20 can generate a vacuum and corresponding upward suction force F2 in the outer tube 10 capable of overcoming an opposite force F3 of a particular fluid 50. For example, high-density fluids may require more volume between the inner tube 20 and outer tube 10 to generate a stronger suction force F2 to overcome the opposite force F3 of a fluid 50. This may require adjusting the offset distance d1 and the volumes of the inner and outer tubes 20 and 10, respectively. Increasing a suction force F1 of the inner tube 20 would increase the rate at which the vacuum and suction force F2 is formed in the outer tube 10. But it would not change the vacuum strength or corresponding suction force F2 in the outer tube, which is a function of the volume between the inner tube 20 and outer tube 10.

As will be discussed below, the outer tube 10 may be designed to have a diameter or width to allow a predetermined volume of fluid 50 to fill the space between the rim 14a of the outer tube 10 and the rim 24a of the inner tube 20 within the outer tube 10. In addition, the offset distance d1 between the rim 14a of the outer tube 10 and the rim 24a of the inner tube 20 may be adjusted to adjust the volume of fluid 50 within the outer tube 10.

When the suction device 100 is used in medical operations, the device 100 may be designed to perform a suction operation for a specific fluid type, such as fat, blood, or saliva, or other fluids, since each type of fluid may have a different known density. Alternatively, the device 100 may be designed to perform a suction operation of a wide range of bodily fluids of varying densities.

When the level of fluid 50 within the outer tube 10 reaches the inlet 24 of the inner tube 20, the outer tube 10 is no longer subject to the suction from the inner tube 20. Instead, the suction F1 of the inner tube 20 is directed only to the fluid 50. The vacuum strength and corresponding suction force F2 within the outer tube 10 remains constant and maintains the fluid 50 level within the outer tube 10. In addition, the suction F1 in the inner tube 20 sucks the fluid 50 toward the outlet 26 and toward a suction base unit or a suction generator connected to the outlet 26.

Figure 2D:
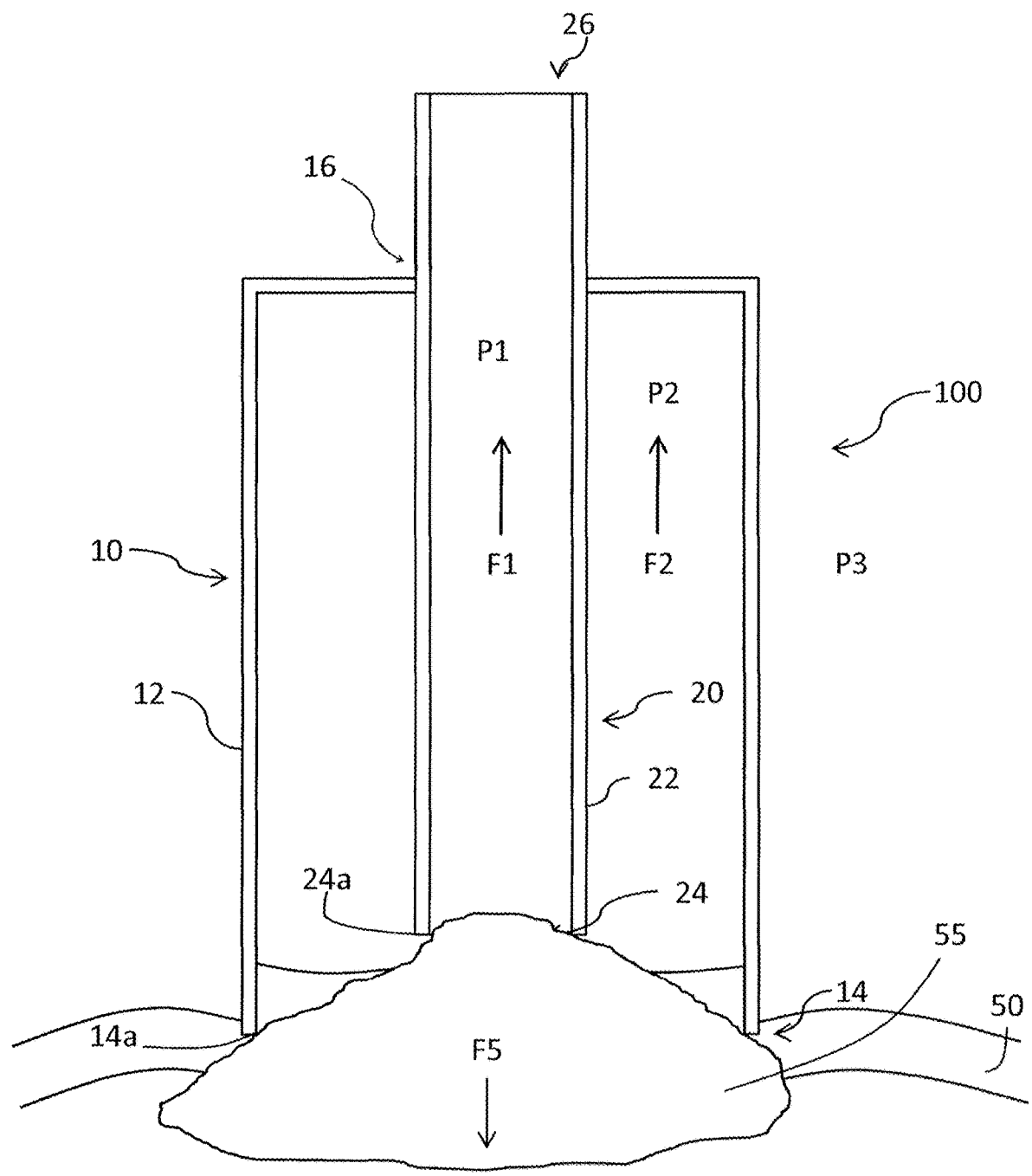
Figure 2E:
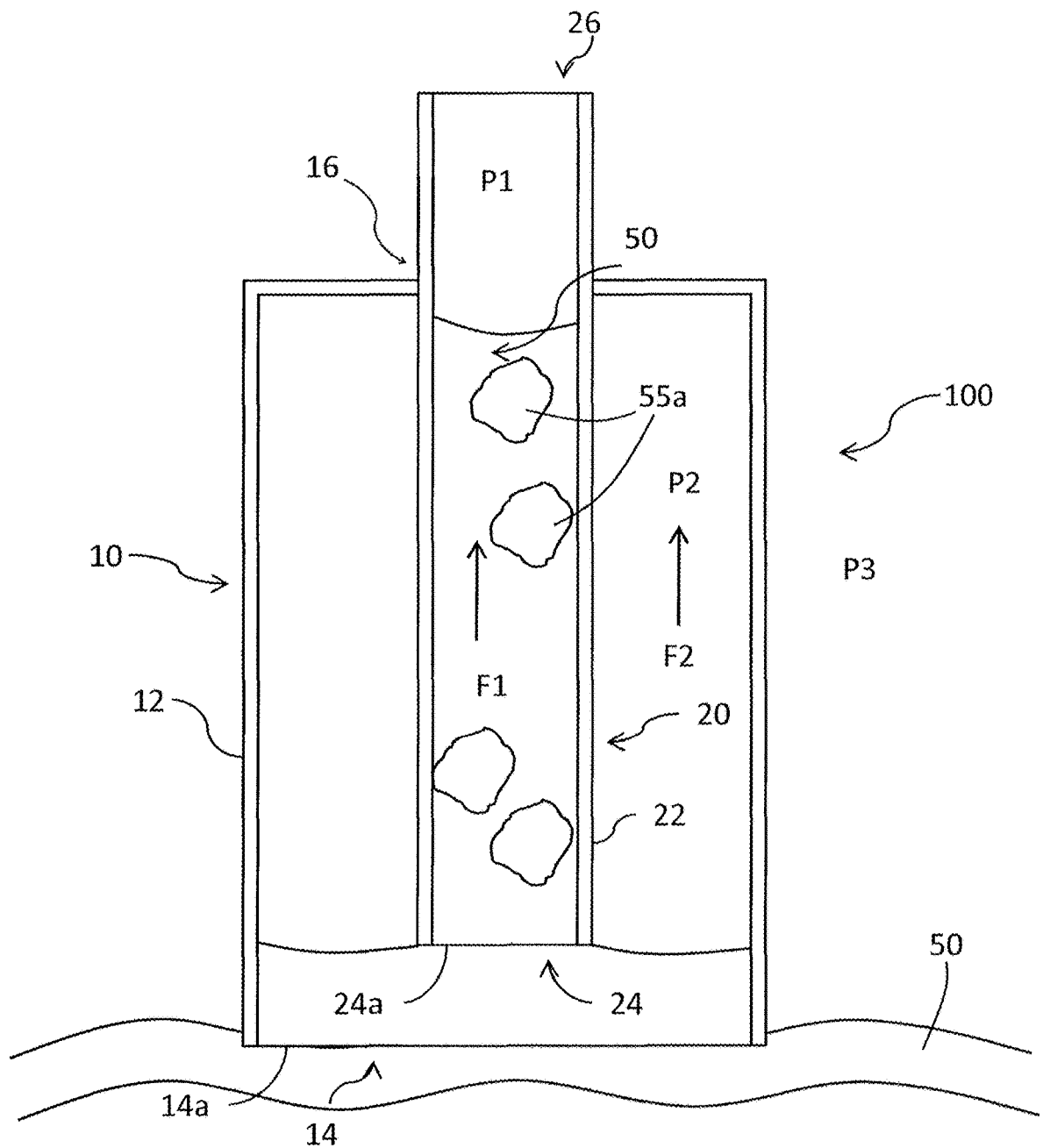

FIG. 2D illustrates a clot 55 blocking the inlet 14 of the outer tube 10 and the inlet 24 of the inner tube 20. Since the outer tube 10 is a vacuum having a low pressure P2 and an upward suction force F2, when the clot 55 blocks the inlets 14 and 24, the vacuum of the outer tube 10 exerts an upward suction force F2 on the clot 55. The suction force F2 of the outer tube 10 combines with the suction force F1 from the inner tube 20 pull the clot 55 to the inlets 14 and 24 of at least one of the outer tube 10 and the inner tube 20, respectively. In other words, the suction force F1 of the inner tube 20 and the suction force F2 of the outer tube combine to form a suction force F4 (F4=F1+F2) that exerts a force on the clot. The combined suction force F4 of the inner tube 20 and the outer tube 10 is greater than the weight F5 of the clot 55, as measured by its volume times its density. The combined suction force F4 of the inner tube 20 and the outer tube 10 is sufficient to destabilize and weaken the clot 55. As illustrated in FIG. 2E, the weakened clot 55 may be broken up into smaller pieces 55a by the combined force F4 of the suction forces F2 and F1 of the outer tube 10 and the inner tube 20 respectively, and the suction device 100 may continue a suction operation without the need to stop the suction operation to clear the inlets 14 and 24.

Thus, as illustrated in the above figures, a suction device 100 may provide suction even when the inner suction tube 20 is blocked or stopped. In addition, the suction device 100 may automatically break up clots or other stoppages by exerting a combined suction force F4 on the clots that is equal to a suction force F1 of the inner tube 20 added to the suction force F2 of the outer tube 10. The combined suction forces and the exertion of suction forces on different parts of the clots or blockages may weaken and break up clots and blockages without the need to stop a suction operation. In addition, the suction force F2 of the outer tube 10 may be generated by the normal suction operation of the inner tube 20.

Figure 3A:
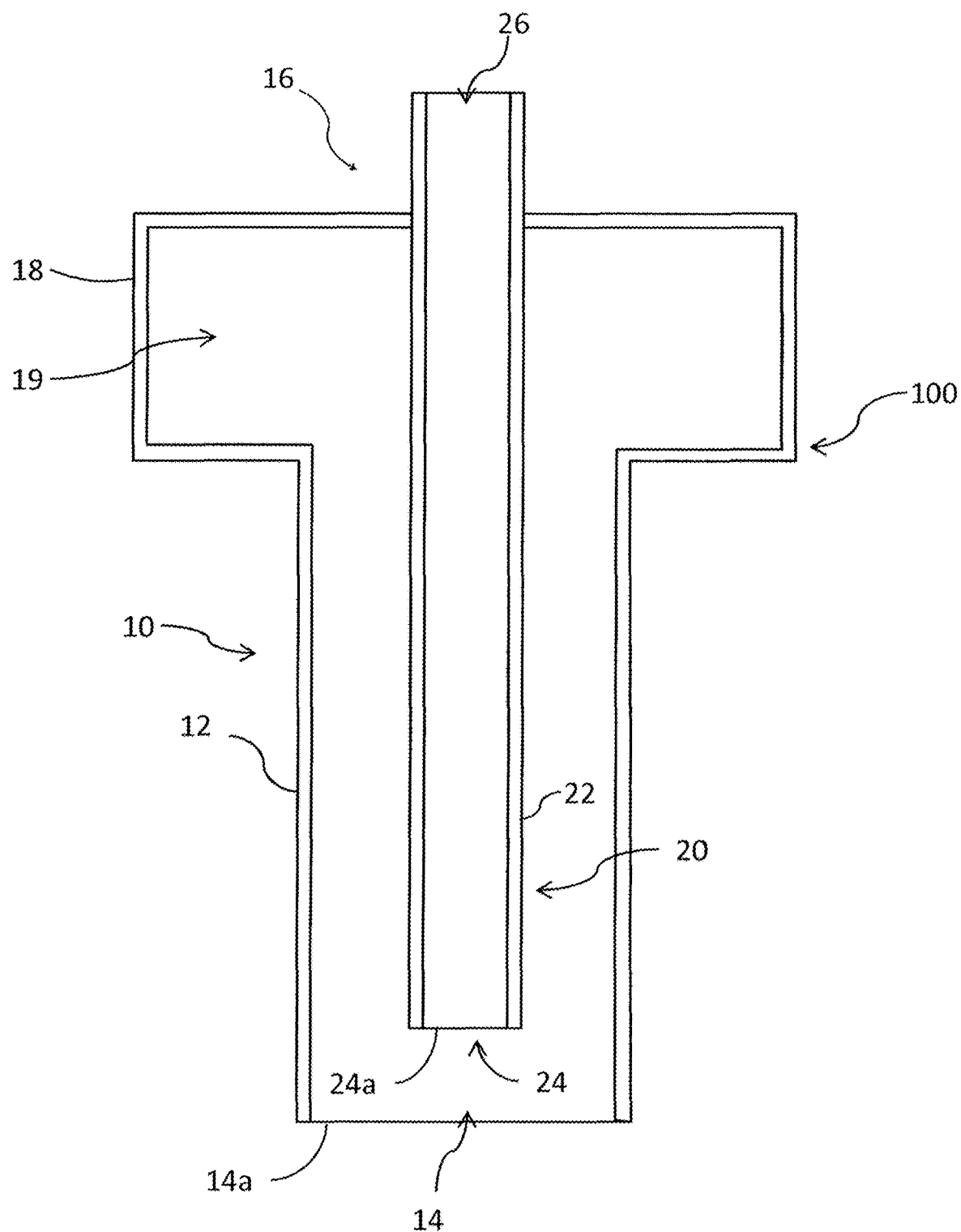
FIG. 3A illustrates a plan view of another embodiment of a suction device according to the present general inventive concept.
Figure 3B:
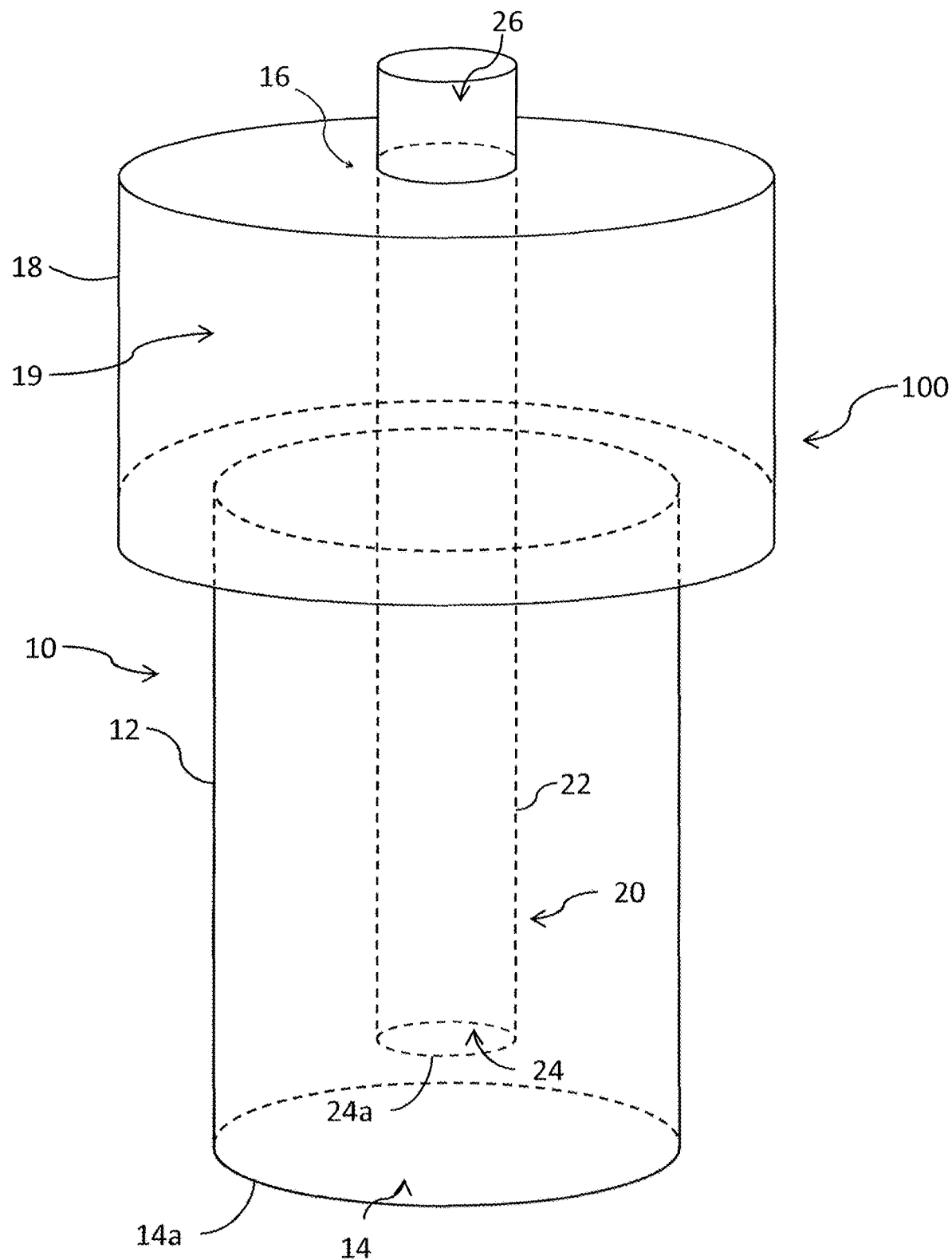
FIG. 3B illustrates a perspective view of the suction device of FIG. 3A.

FIGS. 3A and 3B illustrate a suction device 100 according to an embodiment of the present general inventive concept. The suction device 100 of FIGS. 3A and 3B includes a chamber 19 that is connected to or part of the outer tube 10. The chamber 19 is defined by an outer wall 18 that has a diameter or width that is greater than the diameter or width of the outer tube 10. Since a suction force F2 of the outer tube may be increased by increasing a volume of the outer tube 10, the size of the chamber 19 may be adjusted to increase the vacuum strength and the suction force F2 of the outer tube 10.

While FIGS. 3A and 3B illustrate a chamber 19 having the same center axis as the inner tube 20, the chamber 19 may have an irregular shape and may have a mid-point or center axis that is offset from the midpoint or center axis of the inner tube 20. For example, the chamber may be formed primarily to one side of the inner tube 20 or the outer tube 10.

Although FIGS. 3A and 3B illustrate a chamber 19 having a diameter larger than that of the outer tube 10, the diameter or area of a cross-section of the chamber 19 may be smaller than that of the outer tube 10.

Figure 4A:
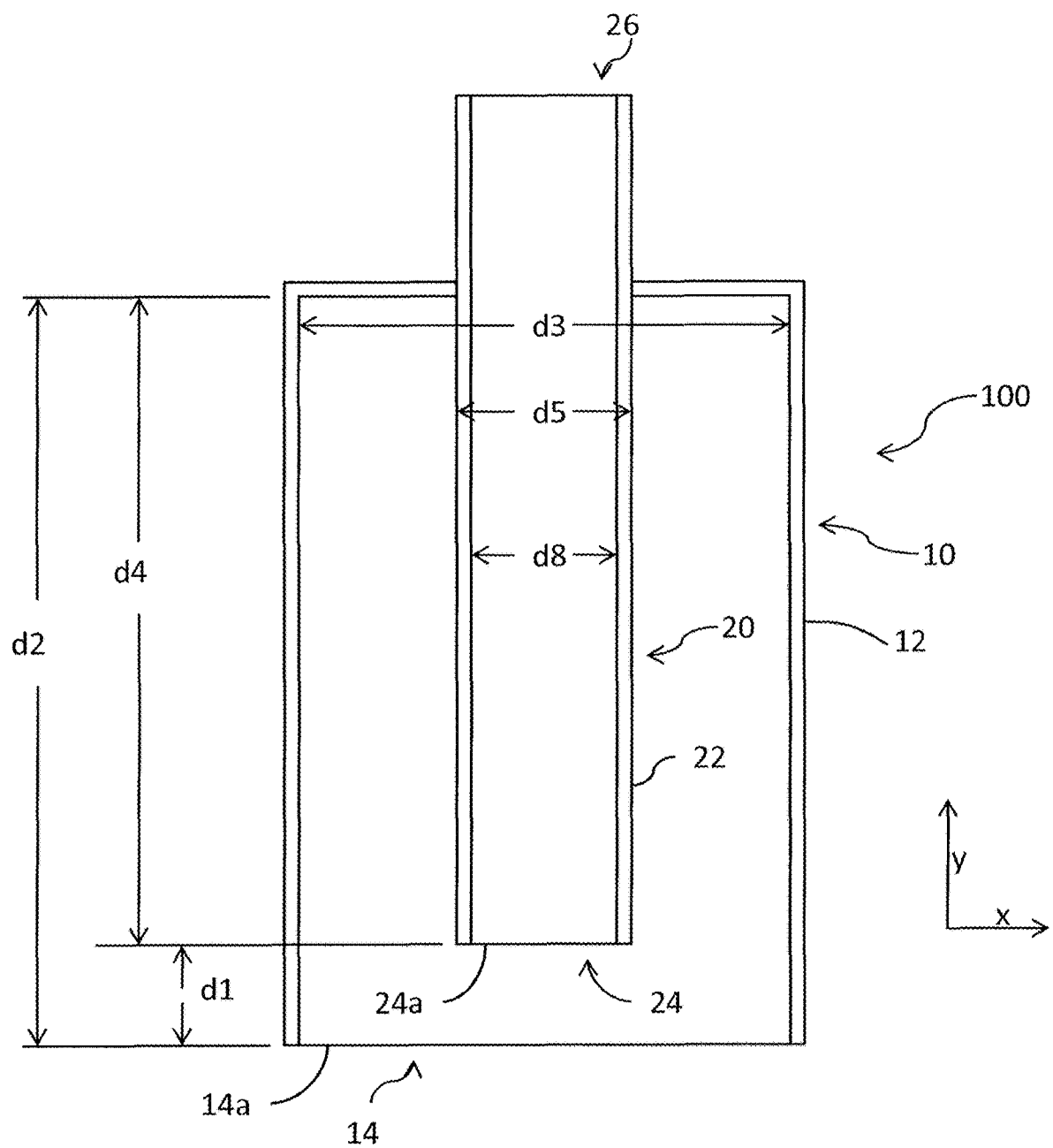
FIGS. 4A and 4B illustrate dimensions of suction devices according to embodiments of the present general inventive concept.
Figure 4B:
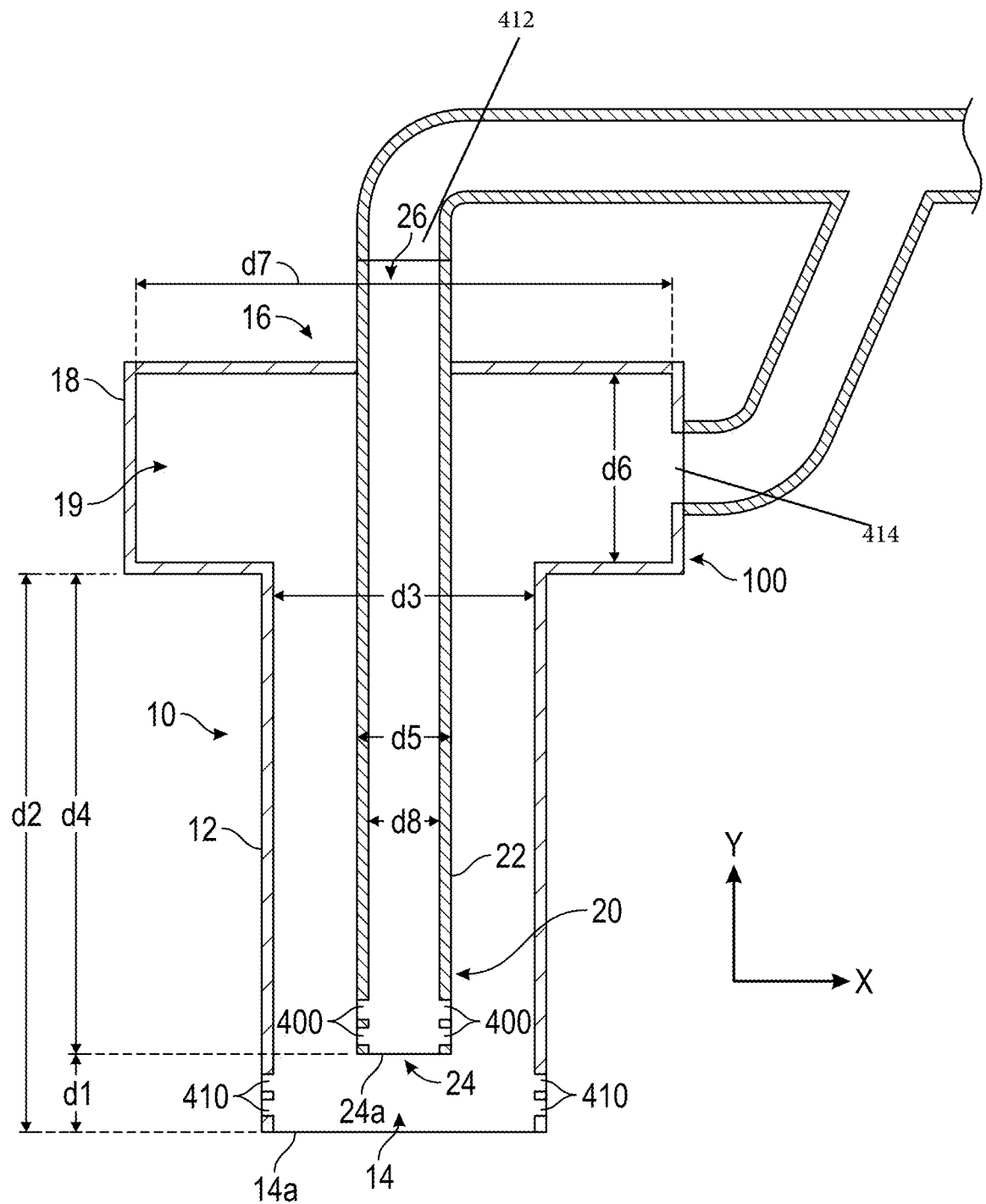

FIGS. 4A and 4B illustrate dimensions of suction devices 100 according to the present general inventive concept. A volume of the outer tube 10 may be adjusted during fabrication by adjusting a width or diameter d7 of the chamber 18, a height d6 of the chamber, a width or diameter d3 of the tube portion 12 of the outer tube 10, a height d2 of the tube portion 12, a width or diameter d8 of the inner tube 20, the outer diameter or width d5 of the inner tube, a height d4 of the inner tube, the offset distance d1 of the rim 24a of the inner tube 20 from the rim 14a of the outer tube 10, or any combination of the above, as shown in FIG. 4A. The volume of the outer tube 10 and inner tube 20 is adjusted to adjust a vacuum strength of the outer tube 10, as described below.

A size, shape, and structure of the suction device may be designed according to a desired use of the suction device. For example, if the suction device is to be used for laparoscopic surgery, the outer tube 10 may have a length between 20 cm and 50 cm and a diameter d3 between 5 mm and 12 mm. The rim 24a of the inner tube 20 may be offset from the rim 14a of the outer tube 10 by at least 2 mm, for example by 5 mm, and the inner tube 20 may have a diameter that is 2-3 mm smaller than the diameter of the outer tube 10. The vacuum chamber 18 may have a volume between 10 ml and 60 ml. The projections at the rim 14a of the outer tube 10 may have lengths of 2 mm, may be spaced 2-3 mm from each other, and there may be four or more projections (See FIGS. 10A to 10D).

When the suction device is used in a surgery requiring a longer incision than laparoscopic surgery (e.g. laparotomy, thorecotomy, etc.) the length of the inner and outer tubes may be less than 30 cm, and the outer and inner tubes may have diameters of 5-10 mm and 3-8 mm, respectively. When the suction device is used in microscopic and other delicate surgeries, such as brain surgery, the length of the outer and inner tubes and the diameter of the tubes may be much smaller than those used in a laparoscopic surgery.

When the suction device is used for liposuction, the length of the tubes may vary depending on the location on the body of the surgery or other circumstances, the outer tube may have a diameter of 6 mm or less and the inner tube may have a diameter of 4 mm or less.

When the suction device is used for nonmedical purposes, the dimensions may vary depending on the density of the fluid to be suctioned. For example, higher density fluids with high-density clots may require a larger vacuum volume to generate a stronger suction force F2 capable of breaking the clot and suctioning the fluid.

Referring to FIGS. 4A and 4B, a pressure P1 within the inner tube 20 may be controlled by a suction base and by the dimensions of the inner tube 20. For example, a suction base that generates a constant suction force on the inner tube will generate a stronger suction force in an inner tube 20 having a smaller inner diameter d8.

The ability of the inner tube 20 to generate a vacuum in the outer tube 10, and of the outer tube 10 to suck a fluid from the rim 14a of the outer tube 10 to the rim 24a of the inner tube 20 depends in part upon the distance d1 between the rims 14a and 24a. For example, if the distance d1 is zero, or if the rim 14a is co-planar with the rim 24a, the inner tube 20 may not be able to generate a vacuum in the outer tube 10. As mentioned above, in some medical operations, an offset distance d1 of at least 2 mm may be used.

The ability of the inner tube 20 to generate a vacuum in the outer tube 10, and of the outer tube 10 to suck a fluid from the rim 14a of the outer tube 10 to the rim 24a of the inner tube 20 may also depend upon the diameter d3 of the tube portion 12 of the outer tube 10. If the diameter d3 of the tube portion 12 of the outer tube 10 is too large, then a volume of a liquid at a bottom of the outer tube 10 may be too large, and the weight F5 (based on volume times density) of the liquid in the bottom of the outer tube may be greater than the suction force F1 of the inner tube 20. Consequently, the fluid 50 may not rise to the inlet 24 of the inner tube 20 from the inlet 14 of the outer tube 10.

The vacuum strength and the corresponding suction force F2 of the outer tube 10 may be adjusted by adjusting the volume of the outer tube 10 and inner tube 20. This may be accomplished by adjusting a width or diameter d7 of the second chamber 18, a height d6 of the chamber, a width or diameter d3 of the tube portion 12 (first chamber) of the outer tube 10, a height d2 of the tube portion 12, a width or diameter d8 of the inner tube 20, the outer diameter or width d5 of the inner tube, a height d4 of the inner tube, the offset distance d1 of the rim 24a of the inner tube 20 from the rim 14a of the outer tube 10, or any combination of the above.

For example, if the length d2 or diameter d3 of the tube portion 12 of the outer tube 10 is increased, the volume of the outer tube 10 increases accordingly, and a vacuum strength and suction force F2 may increase accordingly. The length d4 of the inner tube 20 within the outer tube 10, and the corresponding offset distance d1, may also affect a vacuum strength of the outer tube 10. For example, when the length d2 of the outer tube is fixed and the length d4 of the inner tube 20 decreases, the vacuum strength and corresponding suction force F2 of the outer tube may decrease accordingly.

As illustrated in FIG. 4B, the volume of the chamber 19 may be added to the volume of the lower tube portion of the outer tube 10 to determine a total volume of the outer tube 10. The volume of the chamber 19 may be increased to increase a total suction force F2 of the outer tube 10 without increasing the overall length of the outer tube 10 more than is necessary or desired for a particular application of the suction device 100.

FIGS. 5A to 5E illustrate a suction device 100 having a detachable inner tube 20. If the inner tube 20 may be inserted, removed from, or adjusted in the outer tube 10, the inner tube 20 may include a protrusion 29 to ensure that a rim 24a of an inlet 24 of the inner tube 20 maintains a distance d1 from the rim 14a of the inlet 14 of the outer tube 10. As described above, by maintaining a distance d1 between the rim 14a of the inlet 14 of the outer tube 10 and the rim 24a of the inlet 24 of the inner tube 20, the inner tube 20 may generate a vacuum in the outer tube 10 to more effectively break clots and perform a suction operation.

Figure 5A:
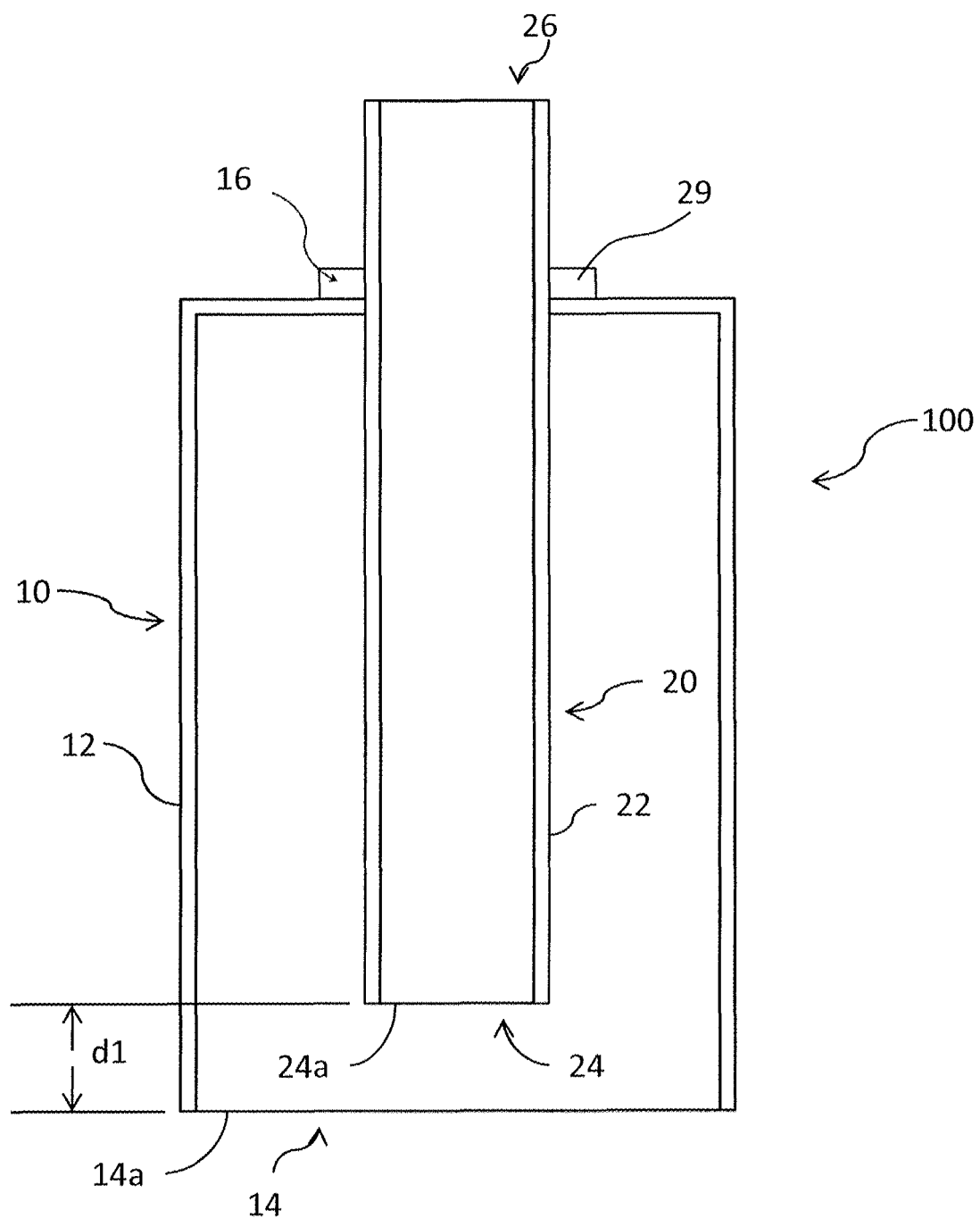
FIGS. 5A to 5E illustrate stopping mechanisms according to embodiments of the present general inventive concept.
Figure 5B:
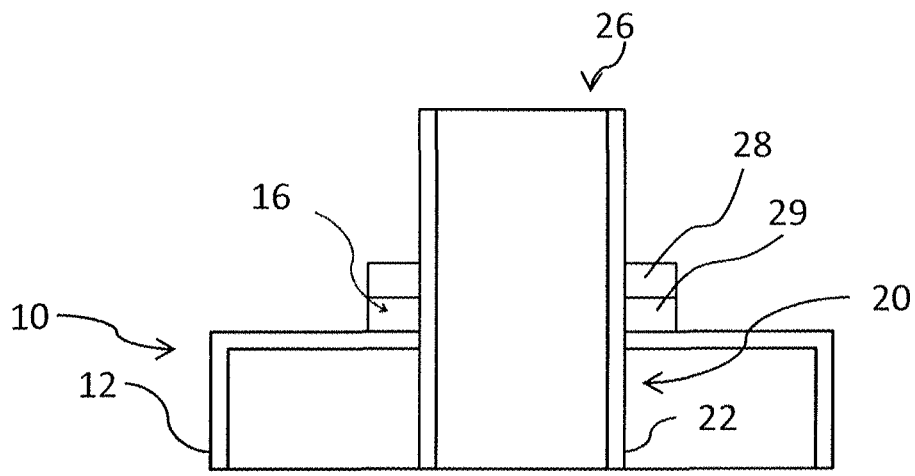
Figure 5C:
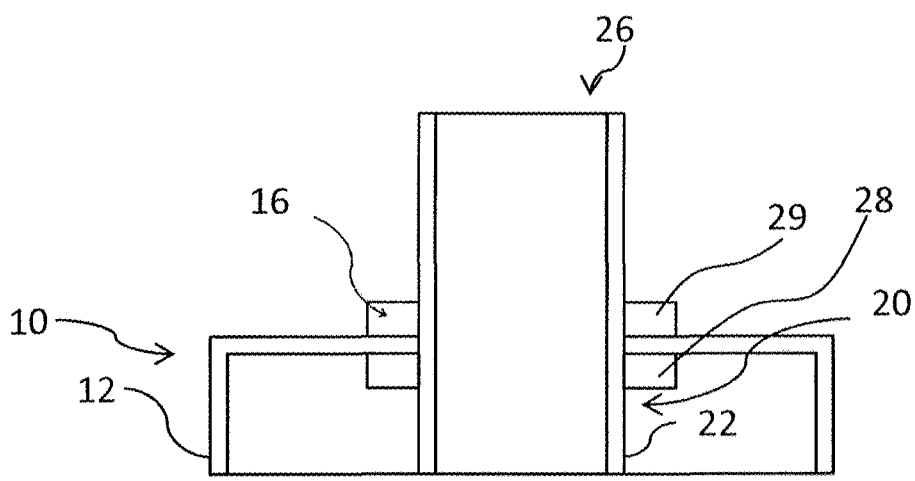

FIG. 5B illustrates an inner tube 20 having a protrusion 29 and a seal 28 located between the protrusion 29 and the upper surface of the outer tube 10. The seal may include an adhesive or weld material to prevent air from entering or exiting the outer tube 10 via the joint 16. FIG. 5C illustrates a seal 28 located on an inside of the outer tube 10.

Figure 5D:
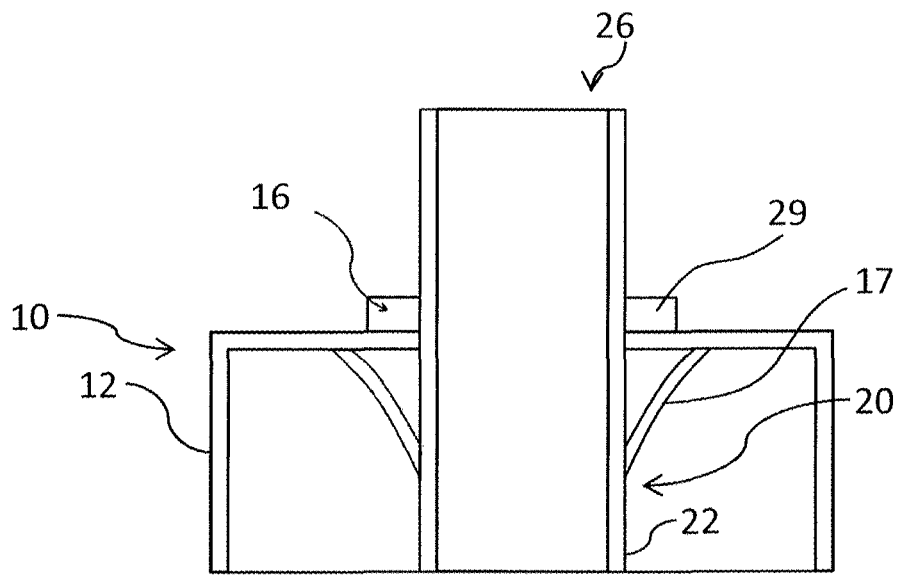

FIG. 5D illustrates a valve 17 fixed to the outer tube 10 to allow the inner tube 20 to be inserted into the opening 16 of the outer tube 10 while preventing air from entering or exiting the outer tube 10. The valve 17 may have a disc shape having a small hole in the center to allow passage of the inner tube 20. The valve 17 may be made of a flexible non-permeable material, such as rubber to prevent the flow of air through the valve material. The seal 28 of FIG. 5B may be combined with the valve 17 of FIG. 5D to improve the air-tight seal of the outer tube 10, for example.

Figure 5E:
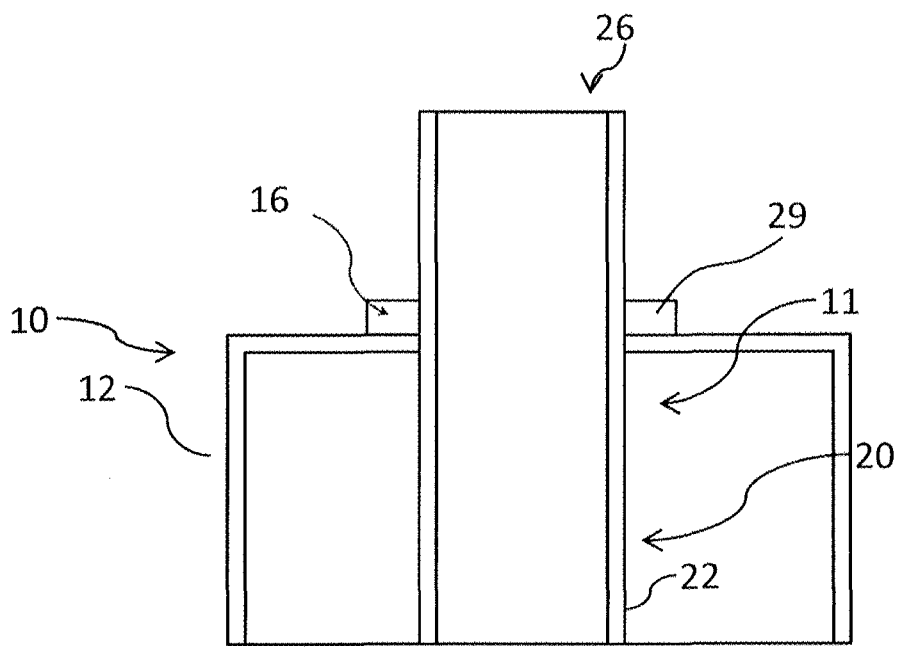

FIG. 5E illustrates an example of an inner tube 20 and an outer tube being connected by a screw portion. For example, the outer tube 10 may include a female portion 11 of a screw and the inner tube 20 may include a male portion of a screw, including protrusions to interact with the female portion to rotate in a spiral manner to connect the inner tube 20 with the inner tube 10.

Although various examples of connections between the inner tube 20 and the outer tube 10 have been presented above, any appropriate connection may be used to secure the inner tube 20 to the outer tube 10 and to generate an air-tight connection between the inner tube 20 and the outer tube 10.

Figure 6:
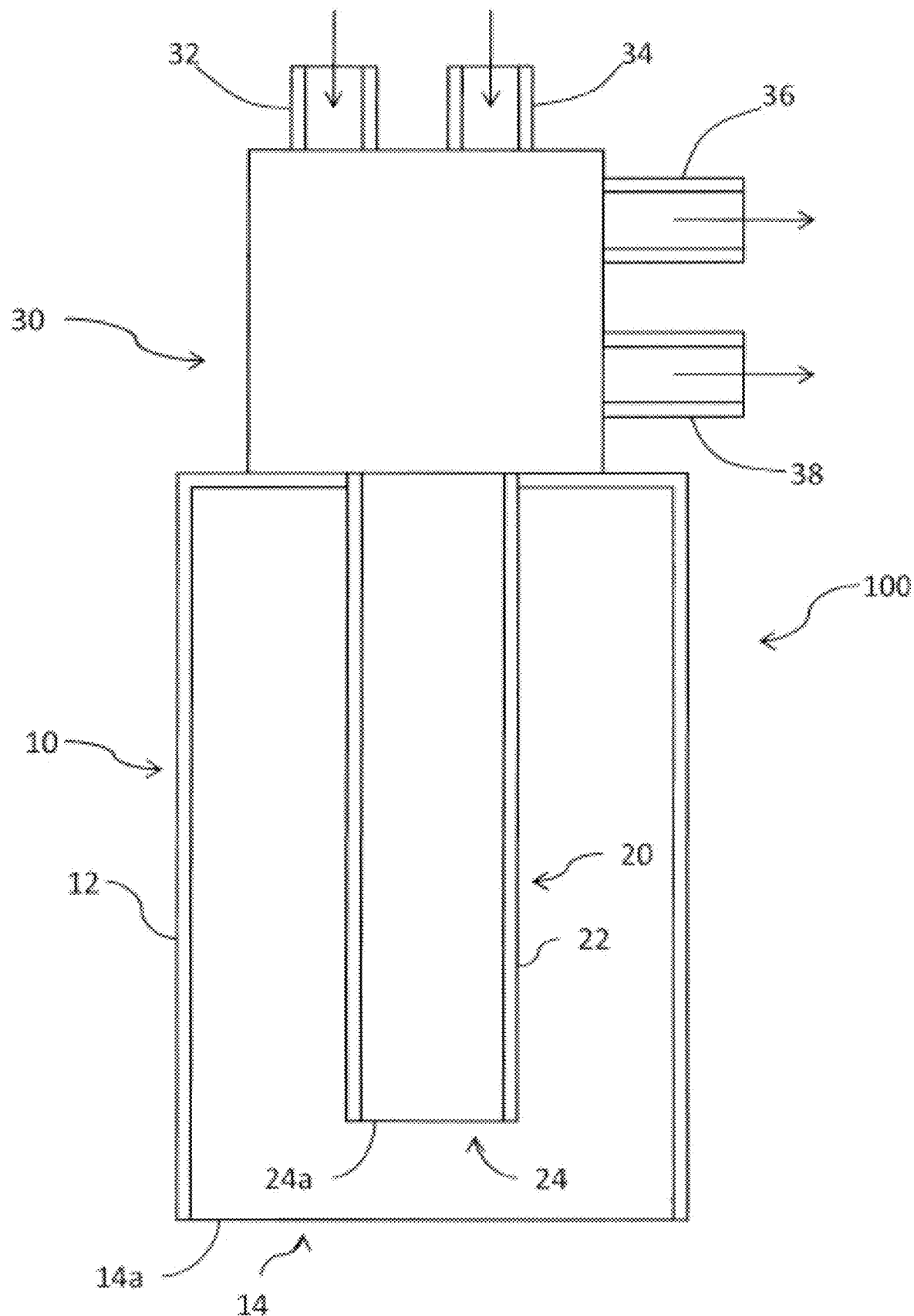
FIG. 6 illustrates a suction device according to another embodiment of the present general inventive concept.

FIG. 6 illustrates a suction device 100 according to an embodiment of the present general inventive concept having a tube fitting 30 connected to the inner suction tube 20. The tube fitting 30 may include one or more inlets 32 and 34 and one or more corresponding outlets 36 and 38. For example, inlet 32 may be a suction inlet to provide air for a suction operation. During a suction operation, the inlet 32 may be connected with the inner tube 20 of the suction device to the outlet 36. Any materials sucked by the inner suction tube 20 during the suction operation may be output from the outlet 36.

The inlet 34 may be an irrigation tube to provide a fluid for an irrigation operation. During an irrigation operation, the irrigation fluid may be output from the inner tube 20 and any excess fluid or fluid that is not output via the inner tube 20 may be output via the outlet 38. Additional inlets and outlets may be included in the tube fitting 30 depending on a desired operation. The tube fitting 30 may be fixed to the inner tube 20, mounted on the upper portion of the outer tube 10, or both. The tube fitting 30 may be permanently fixed or adhered to the inner tube 20 or outer tube 10 via adhesive, welding, or any other device, or the tube fitting 30 may be separable from the inner tube 20 and outer tube 10.

The tube fitting 30 may include one or more inflow control valves and outflow control valves to control a flow of irrigation fluid into the inner tube 20 and air and other fluids out of the inner tube 20.

FIG. 7 illustrates a suction system 1000 including a suction device 100 connected to a suction device base unit 300. The suction device base unit 300 may include various mechanical and electrical modules to perform and support various functions. For example, the suction unit 310 may provide a suction force to the inner tube 20 of the suction device 100 to perform a suction operation. The irrigation unit 320 may provide fluids to the inner tube 20 of the suction device to perform an irrigation operation. The storage 330 may receive any fluid or material from the suction device 100 via the output tubes 36 and 38. For example, if a suction operation results in fluid and clotting material being sucked to the suction device base unit, the fluid and clotting material may be received by the suction unit 310 and stored in the storage 330. The suction unit 310, irrigation unit 320, and storage 330 may include mechanical components including valves, pumps, chambers, and other components necessary to generate a vacuum or suction force, to generate a fluid pressure, or to safely store biological materials.

A control unit 340 may control operation of the various functional modules of the suction device base unit 300. An interface 350 may allow an operator, such as a physician, nurse, surgeon, technician, or other operator to interact with the suction device base unit 300 to control operation of the suction device 100.

Figure 8A:
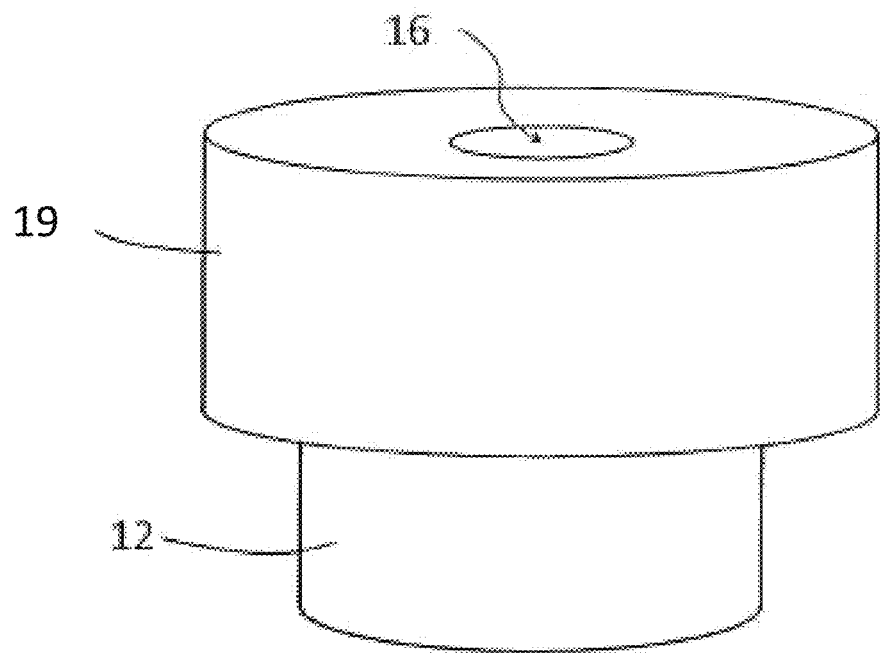
FIGS. 8A and 8B illustrate chambers of an outer tube according to embodiments of the present general inventive concept.
Figure 8B:
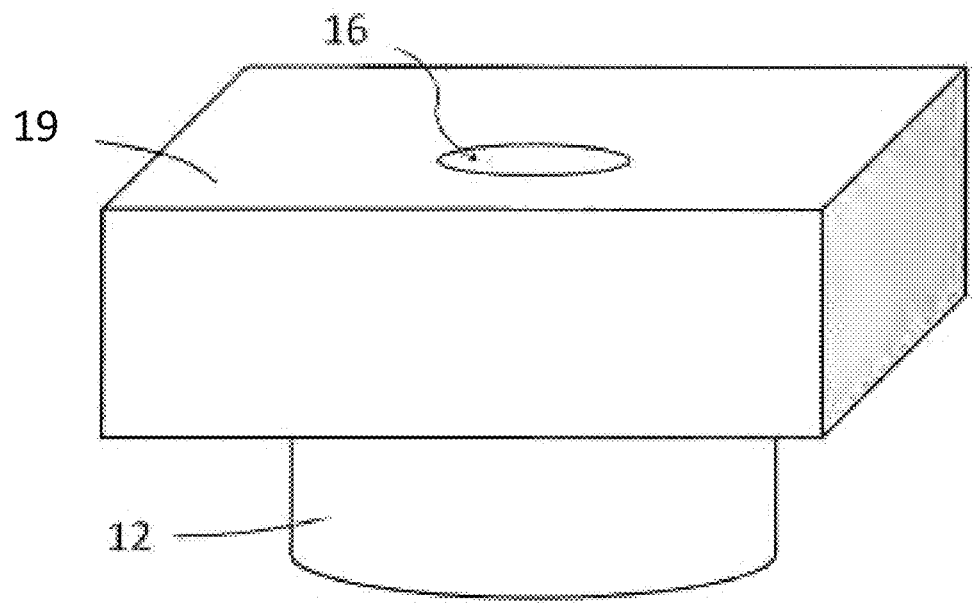
Figure 8C:
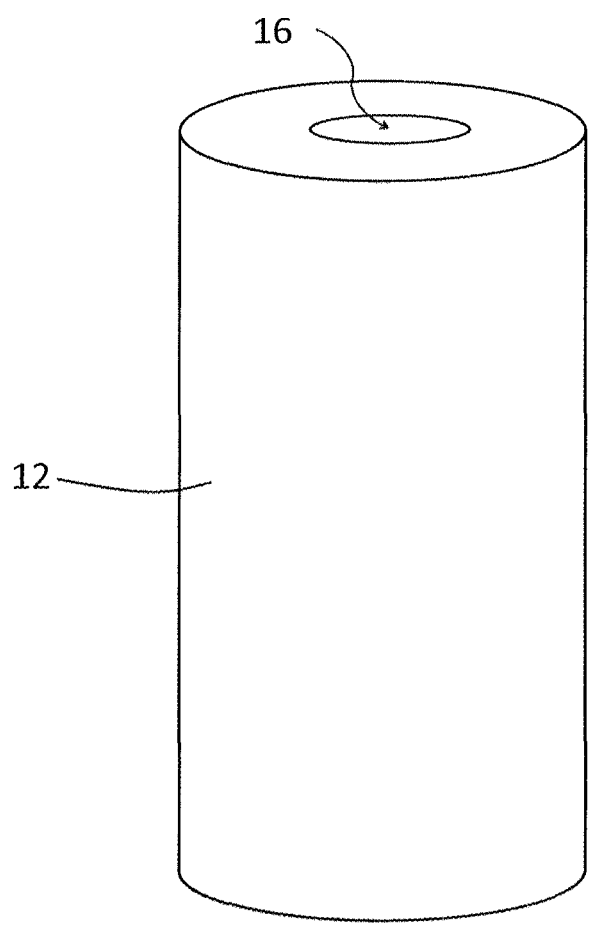
FIG. 8C illustrates an outer tube without a chamber.

FIGS. 8A to 8C illustrate examples of shapes of a chamber of an outer tube 10. In FIG. 8A, the chamber 19 has a cylindrical shape. In FIG. 8B, the chamber 19 has a square or rectangular shape. However, each of the chamber 19, tube portion 12 of the outer tube 10 and tube portion 22 of the inner tube 20 may have any appropriate shape including any desired number of sides. When the suction device is used in medical operations, a rounded shape may be preferred to prevent snagging of the device on tissue. FIG. 8C illustrates an outer tube wall 12 having a cylindrical shape without a chamber 19.

As discussed above, the outer tube 10 may include an opening 16 in an upper surface to receive an inner tube 20, or the inner tube 20 may be formed integrally with the outer tube 10.

Figure 9A:
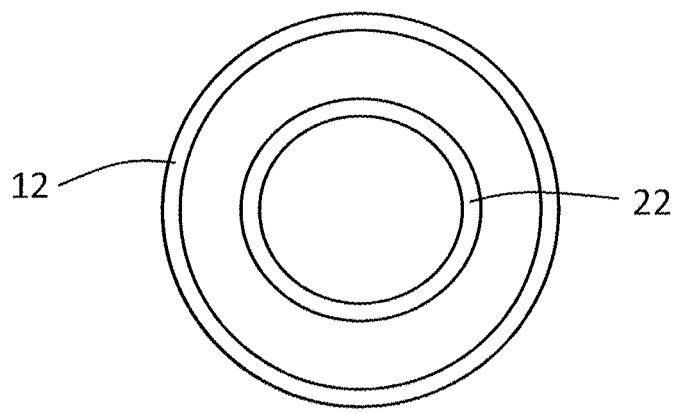
FIGS. 9A and 9B illustrate inner tubes located within outer tubes according to embodiments of the present general inventive concept.
Figure 9B:
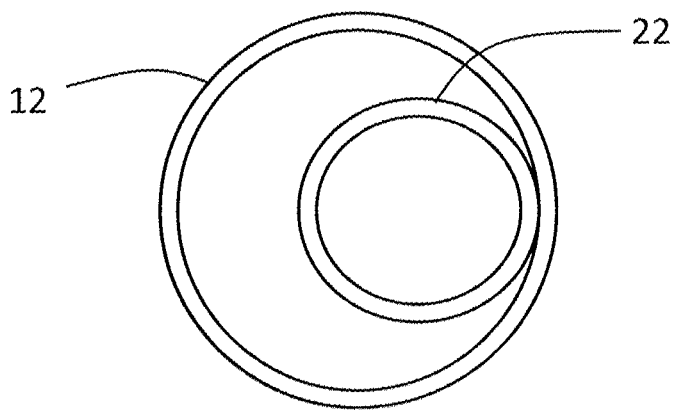

FIGS. 9A and 9B illustrate configurations of the tube portion 22 of the inner tube 20 with respect to the tube portion 12 of the outer tube 10. In FIG. 9A, the tube portion 22 of the inner tube 20 is located at a center of the tube portion 12 of the outer tube. In FIG. 9B, the tube portion 22 of the inner tube 20 is located at a side of the tube portion 12 of the outer tube. The inner tube 20 may be mounted, welded, or adhered to the inner wall of the outer tube 20 and to an upper end of the outer tube 20, as illustrated in FIG. 1A, for example. Alternatively, the inner tube 20 may be separably attached to the outer tube 10. The inner tube 20 may be centered at any position between the center of the outer tube 10 and the side wall of the outer tube 10.

If the inner tube 20 is made of a flexible material, the inner tube 20 may be movable between the walls 12 of the outer tube 10, so that the inner tube 20 may be located in a center area of the outer tube 10 as illustrated in FIG. 9A or against a wall 12 of the outer tube 10, as illustrated in FIG. 9B.

Figure 10C:
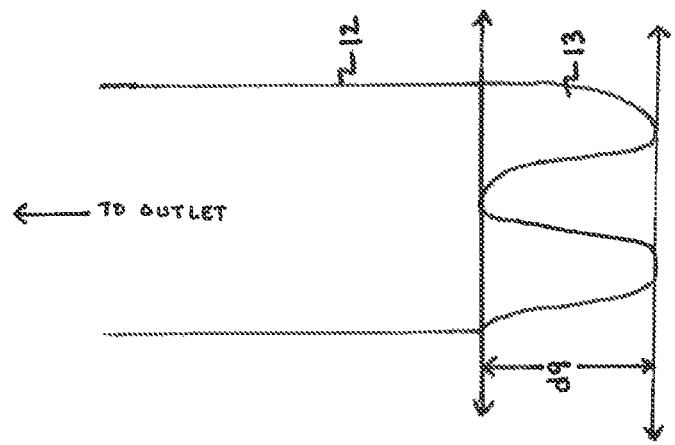
FIGS. 10A to 10D illustrate protrusions of an outer tube inlet according to embodiments of the present general inventive concept.
Figure 10B:
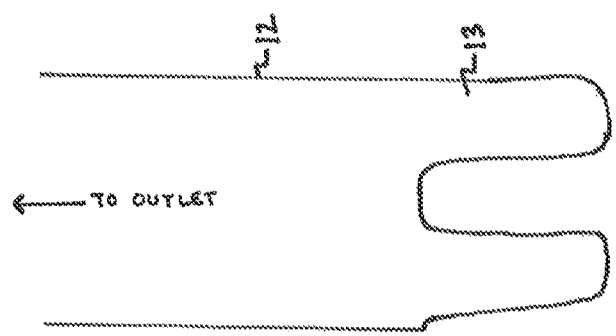

FIGS. 10A to 10D illustrate teeth or protrusions 13 on the rim 14a of the inlet 14 of the outer tube 10. The teeth or protrusions may form a corrugated surface, for example. FIG. 11 illustrates operation of the suction device 100 including the protrusions 13. The protrusions 13 may prevent the suction device 100 from grabbing or tearing tissue when tissue is suctioned at the inlet 14. In other words, as shown in FIG. 11, when fluid 50 rests on tissue 60, and when the inlet 14 of the outer tube 10 of the suction device 100 is rested on the tissue 60 to suck the fluid 50, the protrusions 13 may prevent the tissue 60 from blocking the fluid 50. Instead, the tissue 60 may be held back by the ends of the protrusions 13 while the fluid enters the outer tube 10 via the spaces between the protrusions 13.

Figure 10A:
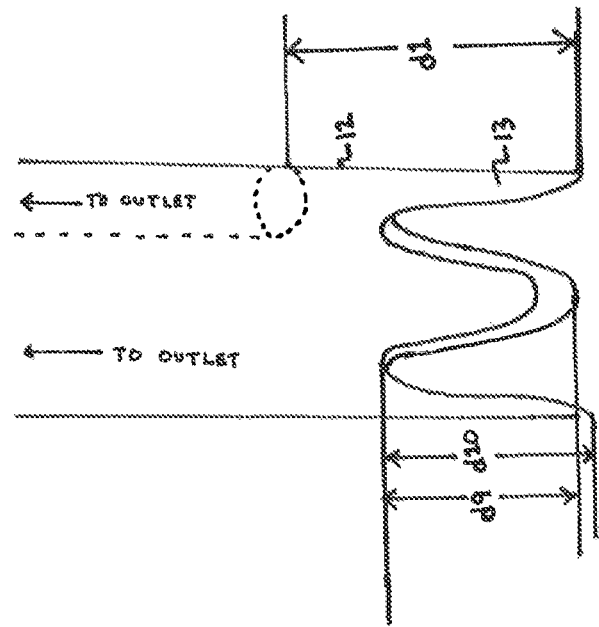
Figure 11:
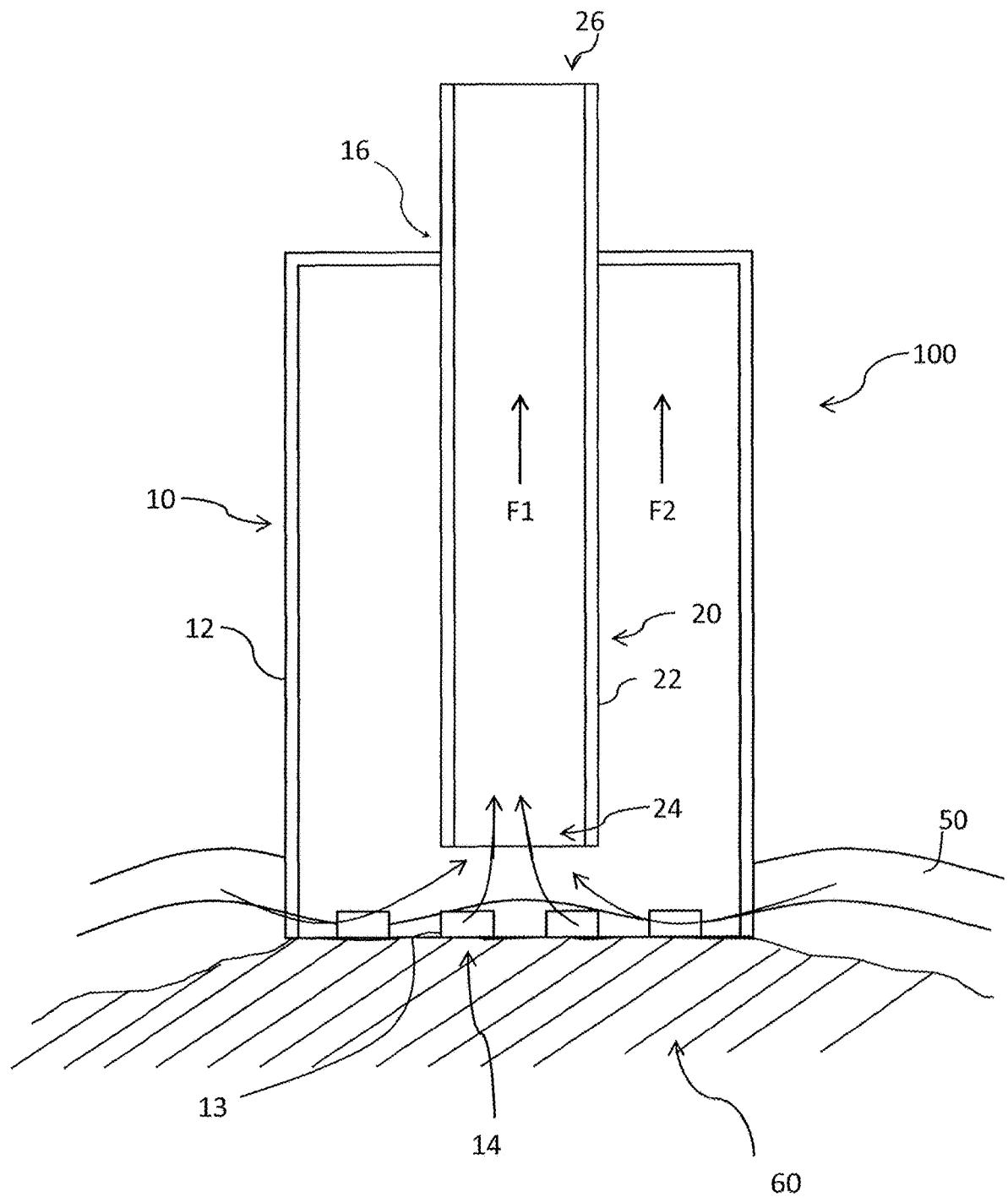
FIG. 11 illustrates an operation of the protrusions of the outer tube intake or inner tube intake according to an embodiment of the present general inventive concept.

FIG. 10A illustrates four protrusions 13 having rounded ends. Two of the protrusions have a first length d9 and two of the protrusions have a second length d10. In other words, a distance between a base of the inlet and a tip of the first set of protrusions is d9, and a distance between a base of the inlet and a tip of the second set of protrusions is d10. The protrusions 13 may have any desired length. However, if the protrusions are too long, the suction device 100 may lose suction. A protrusion length of not greater than 7 millimeters may ensure that the suction device 100 retains suction.

Figure 10D:
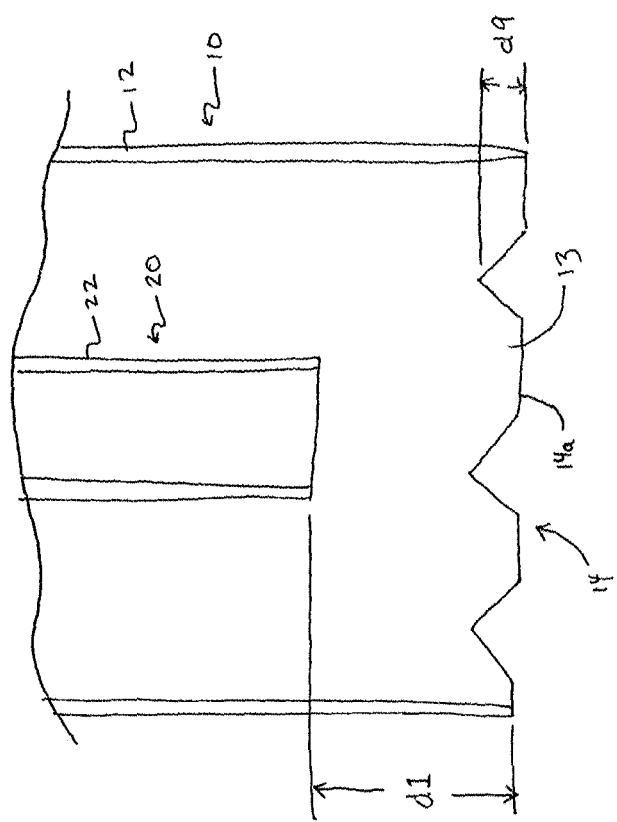

FIG. 10B illustrates protrusions 13 having a square shape with rounded corners to prevent snagging of the corners on tissue. FIG. 10C illustrates protrusions 13 having a rounded tip shape and each of the protrusions has a same height d9. FIG. 10D illustrates protrusions 13 having saw-toothed recesses between them, so that the protrusion has a trapezoidal shape. A distance between a peak of the saw-tooth and an outer surface of the rim 14a defines the height d9 of the protrusions 13.

Figure 10E:
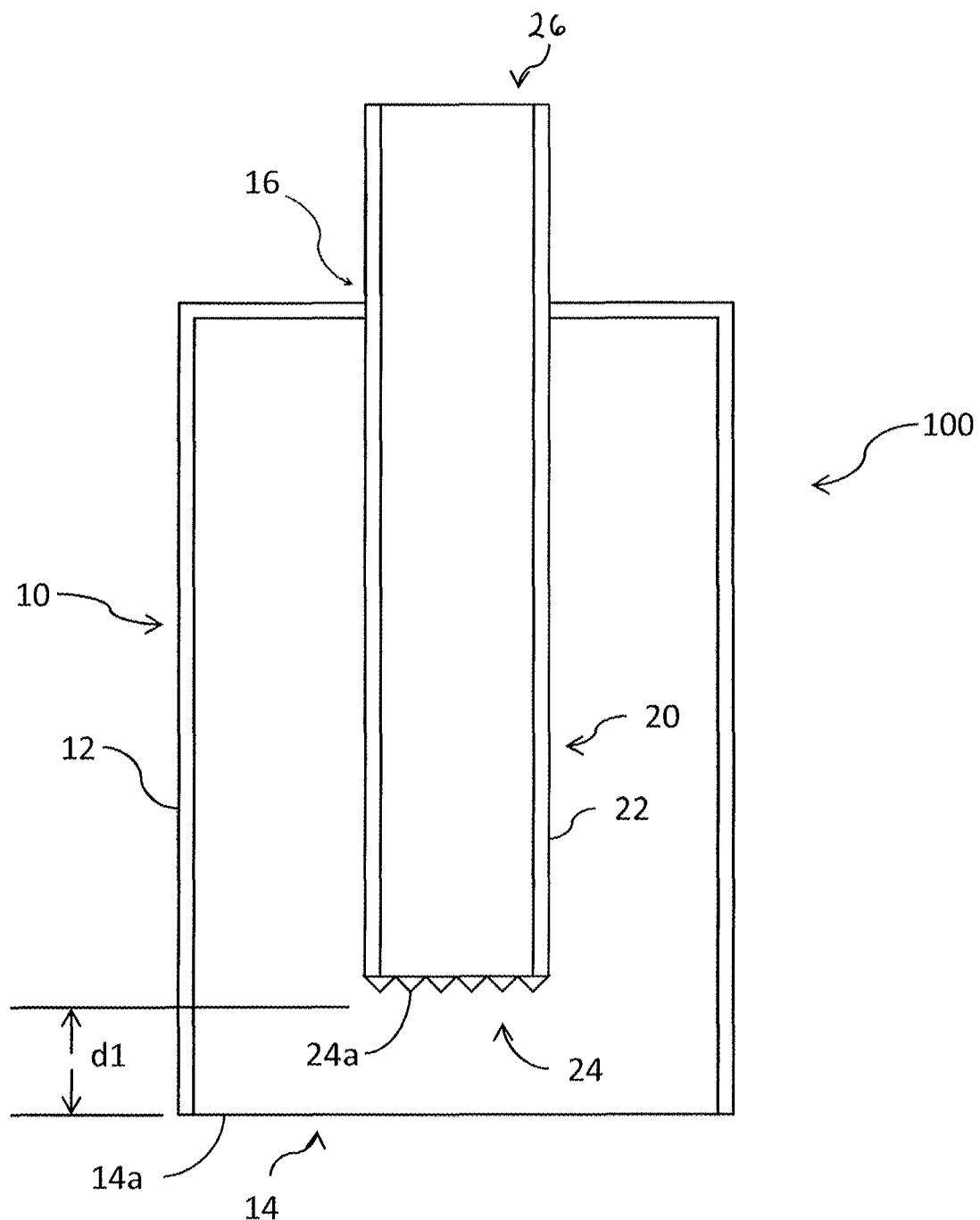
FIG. 10E illustrates protrusions of an inner tube inlet according to an embodiment of the present general inventive concept.

The protrusions 13 illustrated in FIGS. 10A to 10D may also be located on the inner tube rim 24a. In addition, as illustrated in FIG. 10E, since the inner tube rim 24a is separated by a distance d1 from the outer tube rim 14a and thus does not contact tissue, the inner tube rim 24a may include serrated or sharp protrusions, or protrusions having sharp or pointed edges or tips, to further break up clots. The protrusions may have a triangular shape, or any other sharp or pointed shape.

The inner and outer tubes may be made of any appropriate material including metal, plastic, nanofibers, fiberglass, or any other material capable of withstanding suction forces. The type of material used may be adapted to the use to which the suction device is to be put. For example, a suction device that is not to be reused may be made of plastic to be more economically efficient. The inner and outer tubes may be made of the same material or of different materials. For example, the outer tube may be made of plastic, and the inner tube may be made of metal. The inner and outer tubes may be stiff or flexible. When flexible, the tubes may be designed so that the offset distance d1 between the inner tube rim 24a and the outer tube rim 14a is within a predetermined range, even when the tubes are bent.

Figure 12:
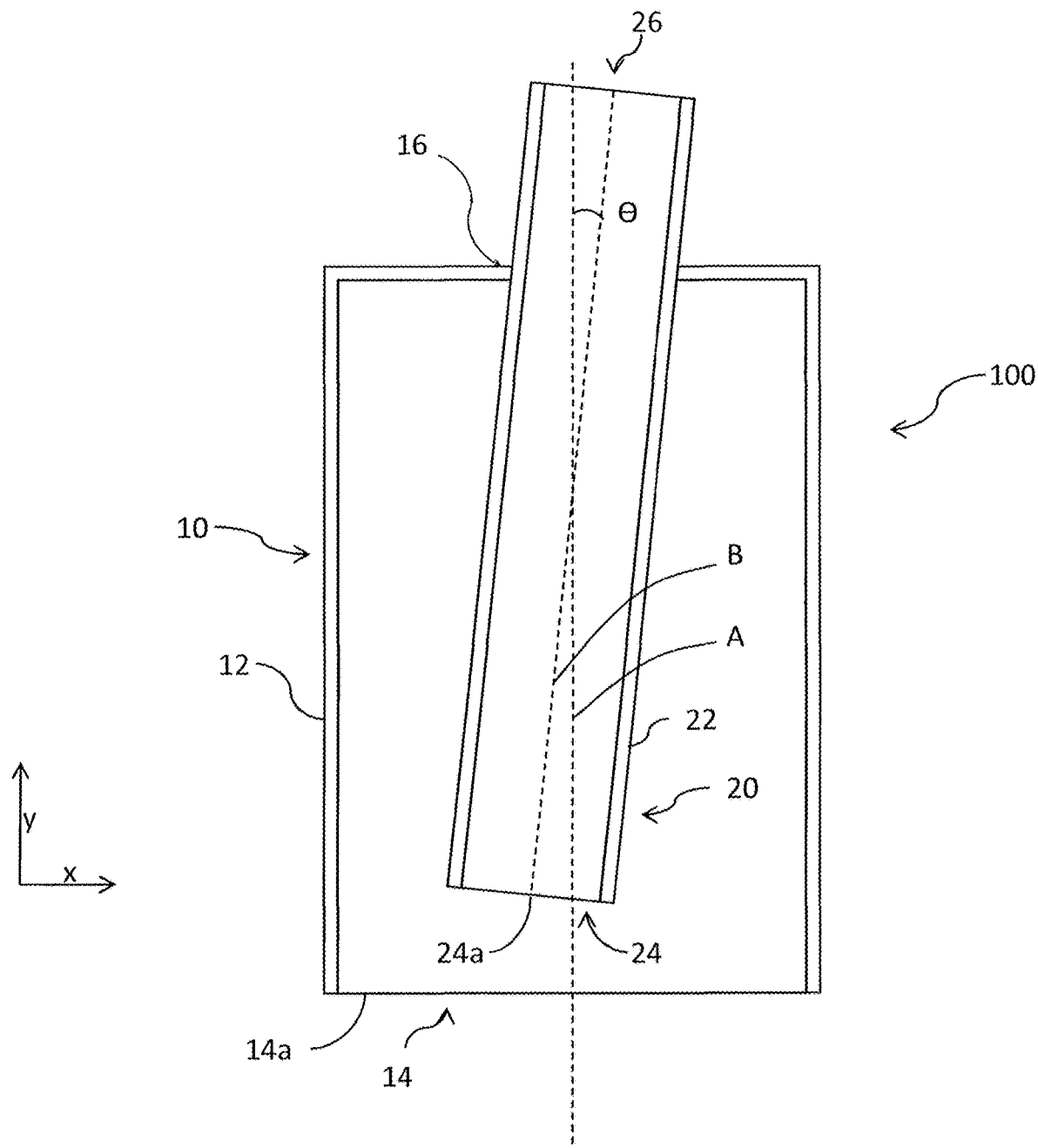
FIG. 12 illustrates a suction device according to another embodiment of the present general inventive concept.

FIG. 12 illustrates a suction device similar to that of FIG. 1A, except the inner tube 20 of the device 100 of FIG. 12 may be mounted at an angle Θ with respect to the outer tube 10. In other words, if the suction device 100 is made so that the inner tube 20 is fixed with respect to the outer tube 10, the inner tube 20 may have a center axis B and the outer tube may have a center axis A, and the axis B may differ from the axis A by an angle Θ. Alternatively, if the inner tube 20 is formed separately from the outer tube 10 but connectable to the outer tube 10, then the inner tube 20 may be designed to move within the outer tube 10. In such a case, the suction device 100 may be designed so that the distance d1 of the inlet 24 from the inlet 14 is maintained even when the inner tube 20 moves within the outer tube 10. In addition, the suction device 100 may be designed so that the inner tube 20 may only move up to a predetermined angle Θ with respect to the center axis A of the outer tube 10 to ensure proper operation of the suction device. The angle Θ of the inner tube 20 may be adjustable with respect to the center axis A of the outer tube 10.

Figure 13:
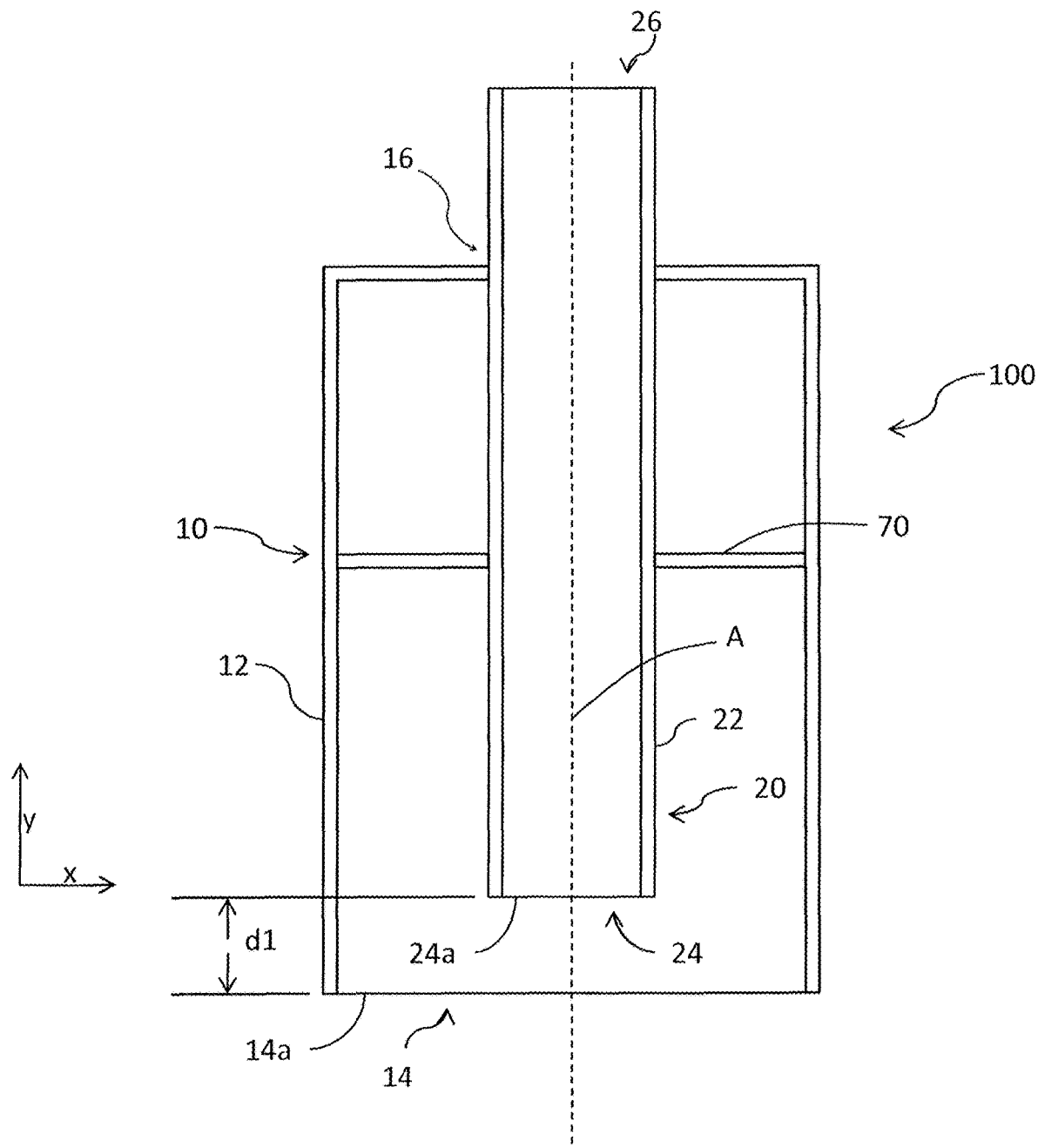
FIG. 13 illustrates a suction device including spacers according to another embodiment of the present general inventive concept.

FIG. 13 illustrates a suction device 100 including one or more spacers 70 to prevent movement of the inner tube 20 with respect to the outer tube 10. The spacers 70 may be formed on the inner tube 20 or the outer tube 10, or they may be attached to the inner or outer tube 20 or 10 after the inner tube 20 is inserted into the outer tube 10. The spacer may include tabs, a disc, linear supports, or any other appropriate shape that prevents the inner tube from moving in a direction x with respect to the outer tube 10 without hindering the suction operation of the suction device 100. In addition, spacers may include holes to maintain open a space between the two ends of the outer tube 10 and to maintain the strength of the suction force F2 generated in the outer tube.

Figure 14A:
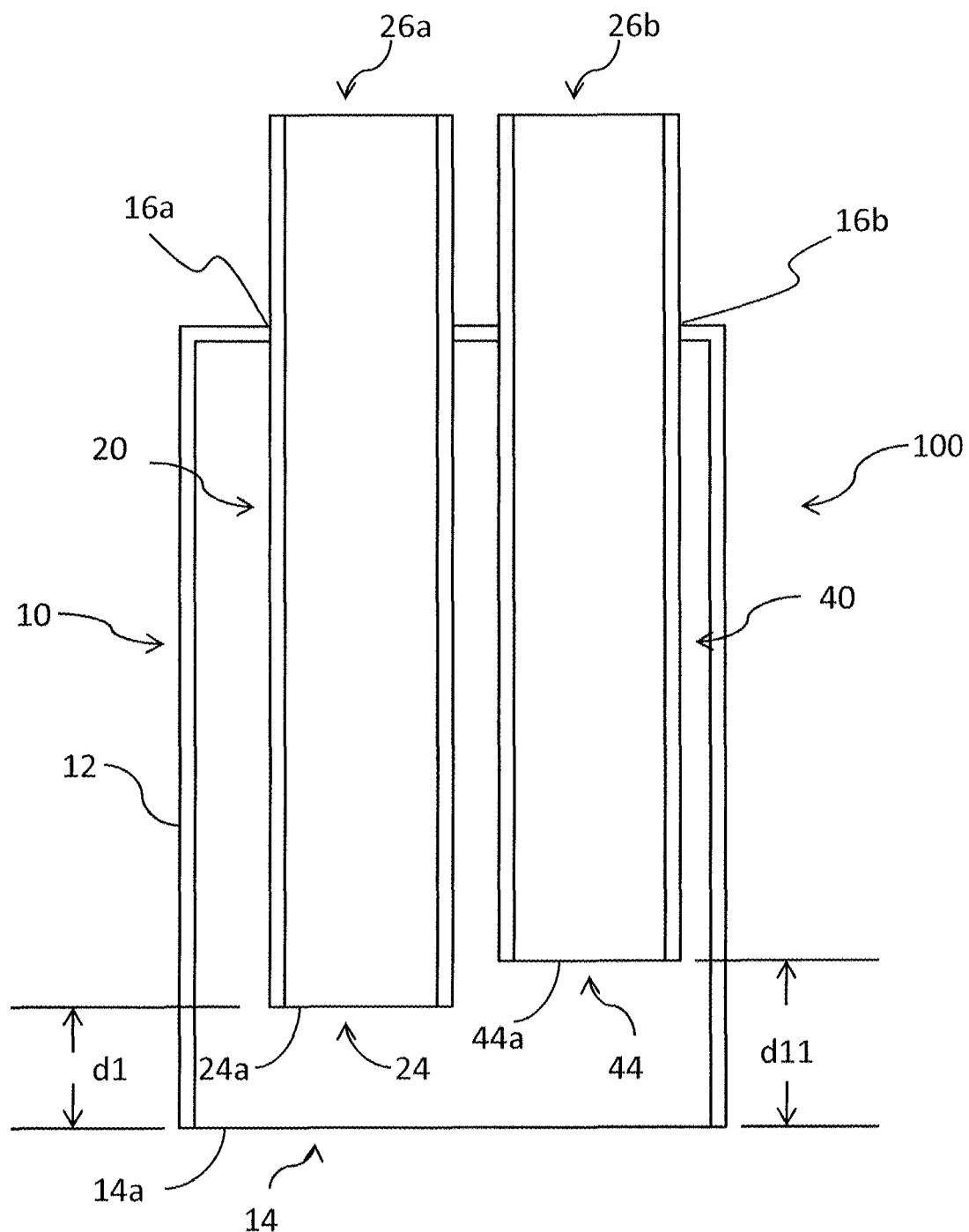
FIGS. 14A and 14B illustrate a suction device having multiple inner tubes according to embodiments of the present general inventive concept.
Figure 14B:
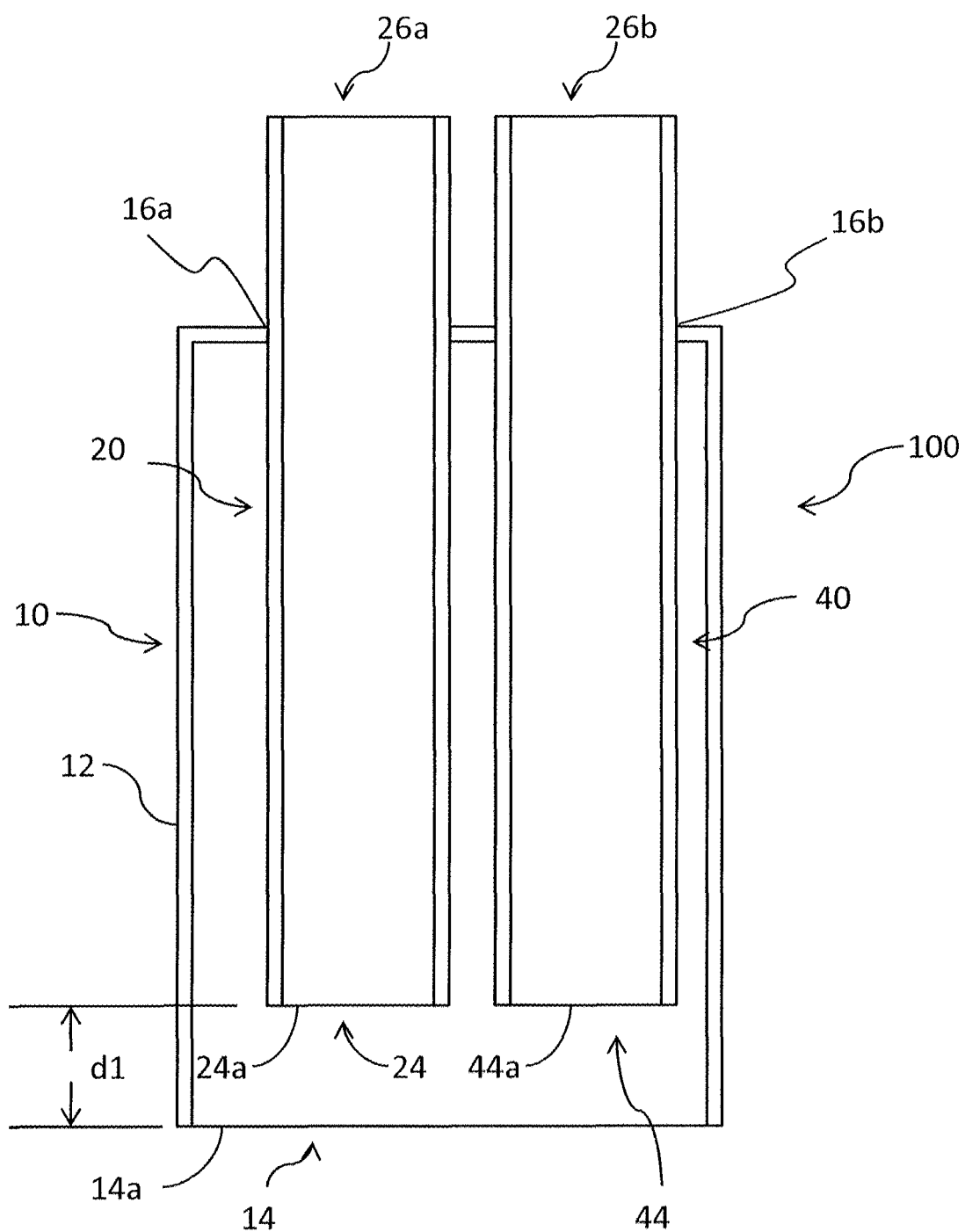

FIGS. 14A and 14B illustrate a suction device 100 according to further embodiments of the present general inventive concept. As illustrated in FIGS. 14A and 14B, the suction device 100 is similar to the suction device 100 described with respect to FIGS. 1A and 1B, for example, but includes two inner tubes 20 and 40 instead of only one. The second inner tube 40 may have an inlet 44 and a rim 44a that is offset by a distance d11 from the rim 14a of the outer tube 10. The distance d11 may be different from the distance d1, as illustrated in FIG. 14A, or it may be the same as d1, as illustrated in FIG. 14B.

The inlet 44 is separate from the inlet of the first tube 24. In addition, the second tube includes an outlet 26b that is separate from the outlet 26a of the first tube 20. The first and second tubes 20 and 40 may be connected to different suction devices, different connectors of the same suction device, or to a same connector of the same suction device. In other words, the first and second outlets 26a and 26b may be connected to each other, may each connect to a same suction tube, or may be entirely separate from each other.

The second tube 40 may provide further suction, may provide a fluid to clean an area of tissue, may be a back-up tube that provides suction only when the first inner tube 20 is blocked, or may provide any other desired function.

The first and second tubes 20 and 40 are each connected to the outer tube 10 at junctions 16a and 16b. As discussed previously, the tubes 20 and 40 may be formed integrally with the outer tube 10 so that the junctions are permanent connections, or the inner tubes 20 and 40 may be insertable and/or removable with respect to the outer tube 10.

According to another variation of the present general inventive concept, more than two inner tubes may be provided. For example, two or more tubes having different offset distances from the inlet of the outer tube may be provided within the outer tube.

Although the figures illustrate inner and outer tubes of a substantially cylindrical shape, the tubes may have any shape, including polygonal or irregular shapes. In addition, the tubes may be bent, twisted, or of irregular diameters (having some portions of a first diameter and other portions of another diameter). For example, both the inner tube and the outer tube may be bent in a lengthwise direction and may be substantially parallel to each other. Accordingly, a center axis of the inner tube 20 at the outlet 26 may be non-parallel with a center axis of the inner tube 20 at the inlet 24.

The material that makes up the inner tube and the outer tube may be either rigid or pliable. For example, the inner tube and/or the outer tube may be bendable to reach an operation location, but may be of a sufficient rigidity to keep a shape of the inlets of the inner and outer tubes.

According to one variation of the present general inventive concept, the inner tube may include holes 400 located in the side walls. The holes 400 may be located at any portion of the inner tube, including near the inlet, towards the center of the inner tube, or near the outlet. However, holes 400 may reduce the suction force F2 that breaks up clots, making the device less effective.

According to another variation of the present general inventive concept, a "Y" connection 412 may be provided to a suction hose. In other words, an outlet 414 may be provided in an upper wall or a side wall of the chamber or the outer tube. The outlet of the outer tube may connect to the outlet of the inner tube to form a single flow path. The tube may be connected to a suction device to generate suction at each of the outlets of the outer tube and the inner tube. However, a Y connection 412 may eliminate the vacuum and suction force F2 in the outer tube, rendering the device ineffective at breaking clots. To maintain the suction force F2 that breaks up clots, the Y connection 412 may include a rotating stop to selectively block the flow path from the outlet of the outer tube. Blocking the inner tube, however, destroys the suction force F2 and renders the device less effective at breaking clots.

Although a few embodiments of the present general inventive concept have been shown and described, it would be appreciated by those skilled in the art that changes may be made in these embodiments without departing from the principles and spirit of the general inventive concept, the scope of which is defined in the claims and their equivalents.

The invention claimed is:

1. A suction device, comprising:
    an outer tube having an open outer inlet at a first outer end; a proximal opening at a proximal end of the outer tube to receive an inner suction tube, wherein the proximal opening is smaller in diameter than an outer inlet diameter of the outer tube; the outer tubing having a constant inner diameter from the proximal end of the outer tube to the first outer end, and the constant inner diameter is equal to the outer inlet diameter; and a wall with an inner surface and an outer surface, wherein the outer inlet is co-axial with a center axis of the outer tube;
        an inner suction tube to be located within the outer tube, the inner suction tube having an open inner inlet having an inner inlet diameter at a first inner end corresponding to the first outer end of the outer tube, an inner outlet at a proximal end of the inner suction tube, and a wall with an inner surface and an outer surface, wherein one or more holes extending through the wall of the inner suction tube are located only near the inner inlet at the first inner end and nowhere else along the wall of the inner suction tube, and the first inner end and the first outer end are open, wherein the inner inlet of the inner suction tube is recessed within the outer tube;
    wherein the outer inlet diameter is greater than the inner inlet diameter;
    and wherein when a suction pressure is applied to the inner outlet at the proximal end of the inner suction tube and the first outer end of the outer tube contacts a fluid or a solid, a vacuum is located in a space directly between a proximal portion of the outer surface of the wall of the inner suction tube and a proximal portion of the inner surface of the wall of the outer tube, as well as within the inner suction tube.

2. The suction device of claim 1, wherein one or more holes through the wall of the outer tube are positioned adjacent to a rim of the outer inlet at the first outer end.

3. The suction device of claim 1, wherein the inner suction tube is configured to perform an irrigation operation.

4. The suction device according to claim 3, wherein the inner suction tube is configured to provide irrigation flowing from the inner outlet towards the inner inlet.

5. The suction device according to claim 1, wherein the outer tube includes a first chamber adjacent to the first outer end and a second chamber with a sidewall proximal to the first chamber; wherein the first chamber is in fluid communication with the second chamber when the device is fully assembled.

6. The suction device according to claim 5, wherein the second chamber includes the proximal opening to receive the inner suction tube.

7. The suction device according to claim 6, wherein the second chamber has a second maximum diameter and the first chamber has a first maximum diameter.

8. The suction device of claim 7, wherein the sidewall has a sidewall outlet.

9. The suction device of claim 8, wherein the inner outlet is in fluid communication with the sidewall outlet through a tube.

10. The suction device according to claim 9, wherein the second maximum diameter of the second chamber is larger than the first maximum diameter of the first chamber.

11. The suction device of claim 9, wherein the inner suction tube includes a stop.

12. The suction device according to claim 1, wherein an offset distance between the inner inlet of the inner suction tube and the outer inlet of the outer tube is adjustable when the device is fully assembled.

13. The suction device according to claim 1, further comprising at least one spacer positioned between the inner suction tube and the outer tube to maintain the position of the inner suction tube with respect to the outer tube.

14. The suction device according to claim 13, wherein the at least one spacer consists of a disc with one or more holes.

15. The suction device according to claim 1, wherein the inner suction tube is configured to be movable with respect to the outer tube.

16. The suction device according to claim 15, wherein the inner inlet of the inner suction tube is retracted within the outer inlet of the outer tube.

17. The suction device according to claim 1, wherein the inner suction tube is removable with respect to the outer tube.

18. The suction device according to claim 1, wherein a rim of the inner inlet of the inner suction tube includes one or more protrusions, the one or more protrusions extending from the inner suction tube in a same direction as a length of the inner suction tube.

19. The suction device according to claim 1, wherein a tab is positioned on the outer surface of the inner suction tube to stop a movement of the inner suction tube in a direction of the outer inlet of the outer tube before a rim of the inner inlet of the inner suction tube reaches a rim of the outer inlet of the outer tube.

20. The suction device of claim 1, wherein no holes are positioned adjacent to a rim of the outer inlet of the outer tube.

* * * * *